(12) United States Patent
Callcott et al.

(10) Patent No.: US 12,324,742 B2
(45) Date of Patent: Jun. 10, 2025

(54) ORTHOPEDIC IMPLANTS HAVING CIRCUMFERENTIAL AND NON-CIRCUMFERENTIAL FIBERS

(71) Applicant: Georgia Tech Research Corporation, Atlanta, GA (US)

(72) Inventors: Trent Callcott, Atlanta, GA (US); David Ku, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 17/374,340

(22) Filed: Jul. 13, 2021

(65) Prior Publication Data
US 2022/0008203 A1     Jan. 13, 2022

Related U.S. Application Data

(60) Provisional application No. 63/050,999, filed on Jul. 13, 2020.

(51) Int. Cl.
*A61F 2/30*     (2006.01)
*A61F 2/38*     (2006.01)

(52) U.S. Cl.
CPC ...... *A61F 2/30756* (2013.01); *A61F 2/30965* (2013.01); *A61F 2/3872* (2013.01); *A61F 2002/30009* (2013.01); *A61F 2002/30069* (2013.01); *A61F 2002/30131* (2013.01); *A61F 2310/00005* (2013.01)

(58) Field of Classification Search
CPC ............... A61F 2/30756; A61F 2/3872; A61F 2/30965; A61F 2002/30009; A61F 2002/30069; A61F 2002/30131; A61F 2310/00005
See application file for complete search history.

(56) References Cited

U.S. PATENT DOCUMENTS

| | | | |
|---|---|---|---|
| 5,116,374 A * | 5/1992 | Stone | A61F 2/3872 435/325 |
| 2005/0159812 A1* | 7/2005 | Dinger, III | A61F 2/0811 623/13.14 |

(Continued)

*Primary Examiner* — Melanie R Tyson
*Assistant Examiner* — Yasniary De La Caridad Morales
(74) *Attorney, Agent, or Firm* — Meunier Carlin & Curfman LLC

(57) ABSTRACT

Embodiments of an artificial meniscus implant are disclosed herein. An artificial meniscus includes at least one circumferential fiber and at least one non-circumferential fiber embedded within an arc-shaped body. The non-circumferential fibers may form loops extending through a peripheral edge of the implant, and the circumferential fibers may extend out of anterior and posterior horns of the implant to terminate in ends that are configured for fixation to bone. The ends may be interconnected, and covered by horn extensions to protect the ends from wear at the bone interface. Methods of making and implanting artificial meniscus are also disclosed herein. The method of making includes stepwise molding, layering, and curing of polymer material around the circumferential fibers and sewing the non-circumferential fibers into the polymer material. Methods of implanting may include threading ends of circumferential fibers through first and second bone tunnels.

20 Claims, 17 Drawing Sheets

(56) References Cited

U.S. PATENT DOCUMENTS

| | | | | |
|---|---|---|---|---|
| 2011/0288199 A1* | 11/2011 | Lowman | ................. | A61L 27/48 |
| | | | | 523/113 |
| 2014/0031933 A1* | 1/2014 | Gatt | ........................ | A61F 2/44 |
| | | | | 623/14.12 |
| 2016/0166389 A1* | 6/2016 | Amis | .................... | A61F 2/3872 |
| | | | | 623/14.12 |
| 2017/0007411 A1* | 1/2017 | Khan | .................... | A61F 2/3872 |
| 2019/0076260 A1* | 3/2019 | McCullen | .............. | A61F 2/3872 |
| 2019/0380838 A1* | 12/2019 | Ghodbane | ............... | A61L 27/48 |
| 2020/0060834 A1* | 2/2020 | McCullen | ........... | A61F 2/30965 |

\* cited by examiner

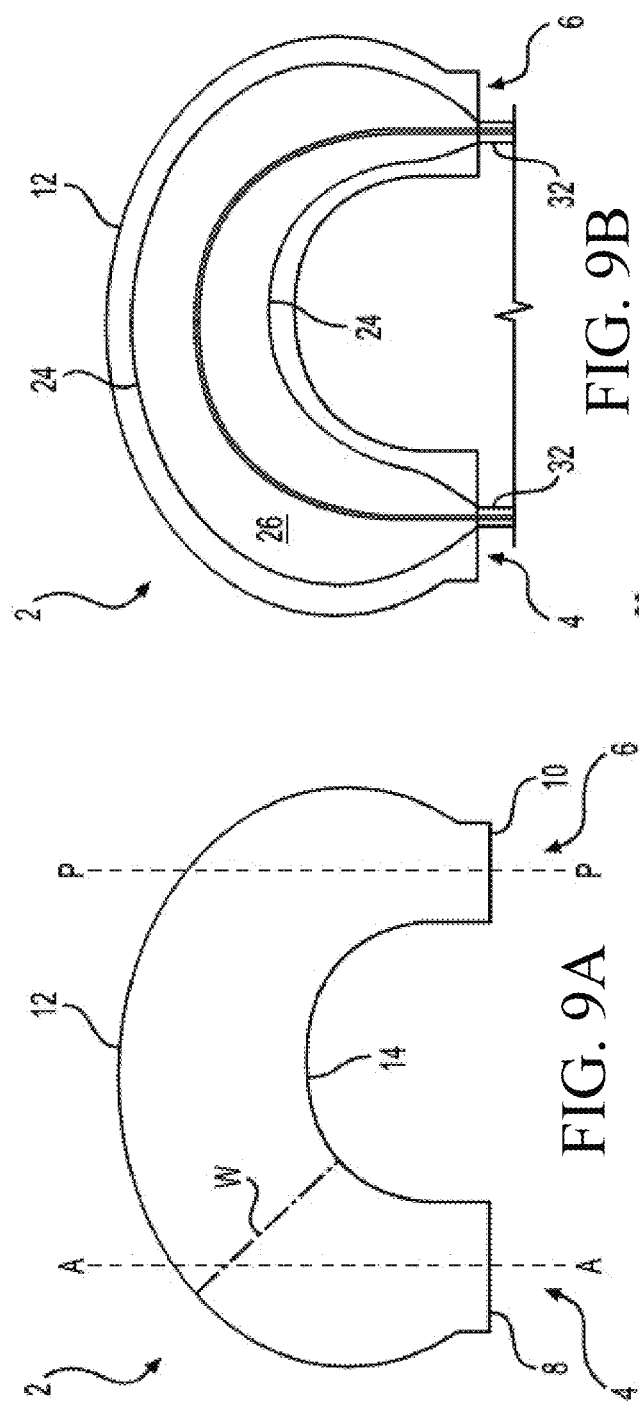
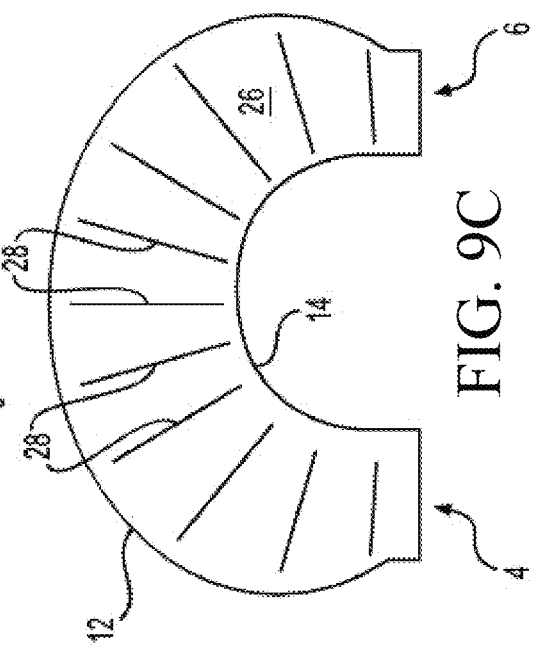

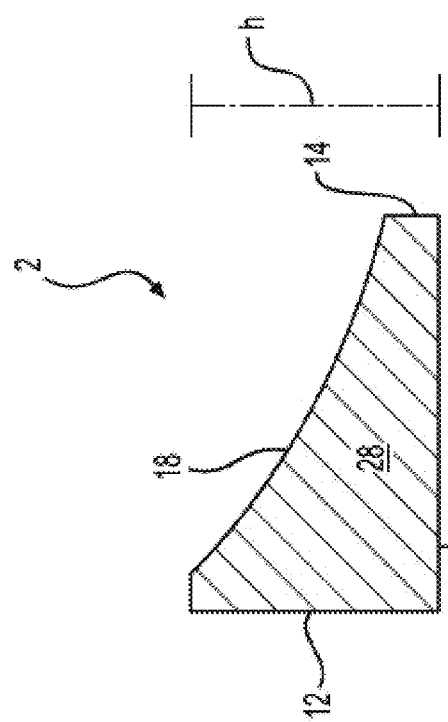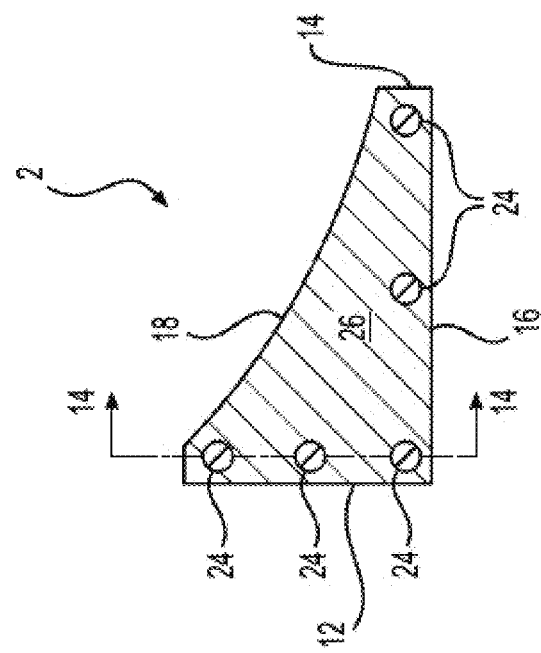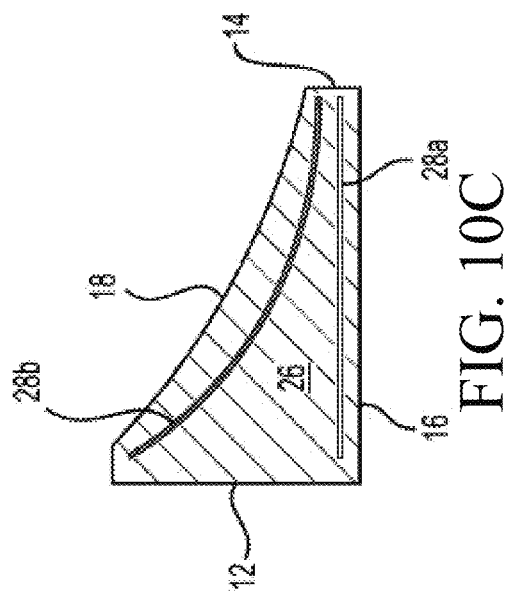
FIG. 10A
FIG. 10B
FIG. 10C

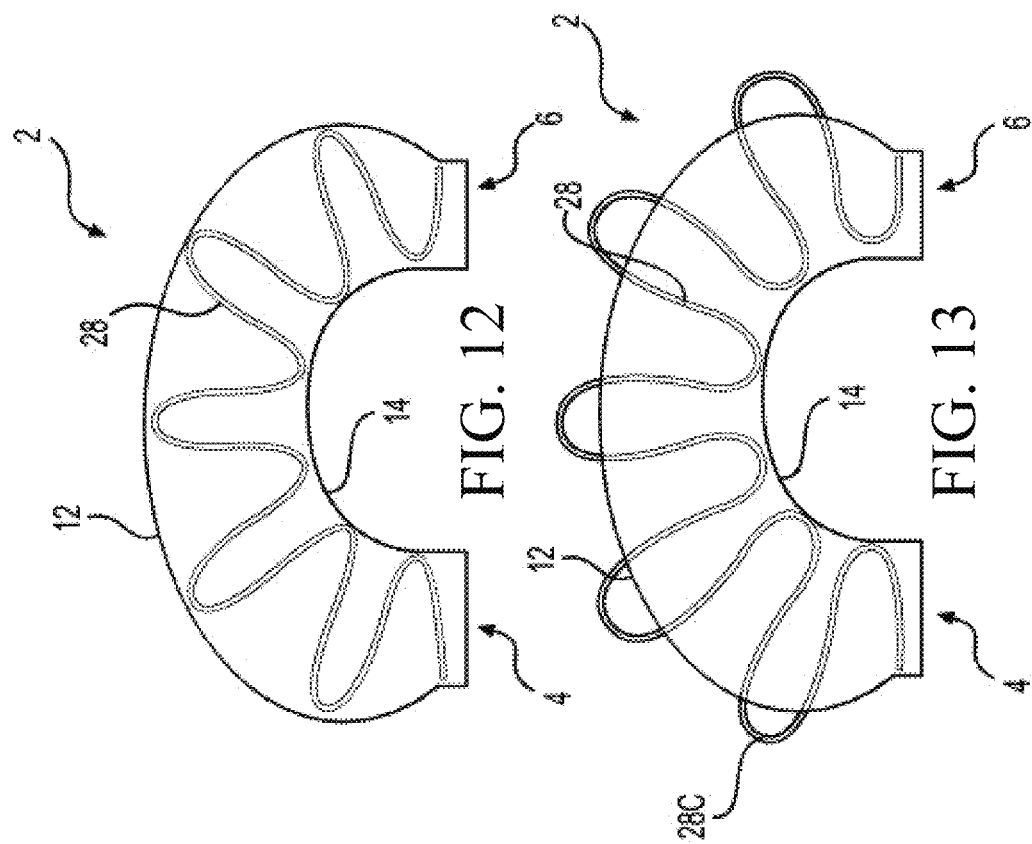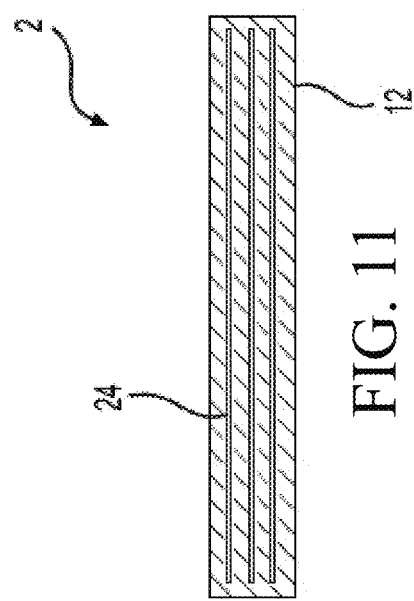

ORTHOPEDIC IMPLANTS HAVING CIRCUMFERENTIAL AND NON-CIRCUMFERENTIAL FIBERS

RELATED APPLICATIONS

This application claims priority to U.S. Provisional Application No. 63/050,999, filed Jul. 13, 2020, which is hereby incorporated by reference in its entirety.

FIELD

This application relates to orthopedic implants, and more specifically, to meniscal implants having circumferential and non-circumferential fibers.

BACKGROUND

The primary functions of the meniscus are load transmission and shock absorption within the knee. The meniscus attempts to accomplish this by mitigating the compressive stress transferred through the knee by distributing this load across a large area. A natural meniscus, which is located between the femur and tibia with one on the lateral and one on the medial side of the knee (see FIGS. 1A-B), typically absorbs 50% to 70% of the load across the knee and increases the tibiofemoral contact area by two to three times. To allow for the greatest possible stress transfer, the meniscus has a curved superior surface to conform to the femoral condyle and a flatter inferior surface to align with the tibial plateau. The natural meniscus includes both a lateral and medial menisci, which have varying shapes and dimensions. The lateral and medial menisci are attached to the tibia at respective meniscus horns (see FIG. 1B), which provides semi-constrained mobility across the tibial plateau to allow for meniscus deformation and load dissipation.

In addition to its shape and position, the structure of the meniscus helps with its ability to dissipate compressive loads and survive the environment of the knee. About 72% of its weight is water, 21% is collagen (90% of this is type I collagen), and the remaining weight is primarily composed of fibrochondrocyte cells, proteoglycans, glycoproteins, and elastin. The collagen fibers contribute directly to the strength and tensile stiffness of the meniscus and are organized in the network shown in FIG. 2. The majority of the fibers are oriented circumferentially within the body of the meniscus as a primary component of its function, which is depicted in FIGS. 3A-3B, which show the loading of the meniscus from the side (FIG. 3A) and from above (FIG. 3B) showing hoop stress development and radial displacement.

Because of the wedged shape of the meniscus, it extrudes radially when compressed. However, excessive radial extrusion is prevented because of the circumferentially oriented fibers and ligaments that attach the meniscus horns to the tibia. This results in tensile hoop stresses in the circumferentially oriented fibers. Radially oriented fibers encompass the bulk of the meniscus. A few radially oriented fibers also appear in the bulk of the meniscus woven through the circumferential fibers. Together, all of these radial fibers help to tie the meniscus together and prevent separation of the circumferential fiber network. Exterior to this layer, the surfaces of the meniscus are composed of a random mesh of fibers that aid in low friction articulation with the contacting articular cartilage.

Even though the collagen structure of the meniscus is fairly uniform across its width, this is not the case for its vascularity. The meniscus contains blood vessels and nerves only in the peripheral 10-25% of the tissue, as shown in FIG. 4. This vascular and neural region is referred to as the red zone and the avascular and aneural region is referred to as the white zone. The healing capacity of each region is directly related to its blood circulation, which results in the majority of the meniscus being susceptible to permanent injury.

Meniscus injuries can be caused due to degenerative tears, which result from cumulative stresses on the tissue. Meniscus injuries may also be traumatic, which can result from axial and shear loads within the knee. FIGS. 5A-5G show examples of the most common types of traumatic tears. Overall, the most common tear types are the bucket handle (23.1%), longitudinal (18.2%), and horizontal (17.4%). Bucket handle and longitudinal tears occur between parallel circumferential fibers. Horizontal tears are thought to result from shear forces between the superior and inferior surfaces and tend to initiate within the body of the meniscus. Longitudinal (22.1%), bucket-handle (32.4%), and oblique (16.8%) tears are the most common for the medial meniscus. Radial (32.7%) and horizontal (25.8%) tears are the most frequent for the lateral meniscus. FIG. 6 shows the most common location of tears. Over 70% of traumatic tears in the medial menisci and over 90% of the traumatic tears in the lateral menisci occur in zones 2 and 3 shown in FIG. 6. This means that the majority of traumatic meniscus tears occur in the avascular region (identified in FIG. 4), which limits natural healing potential.

Known methods of repairing meniscus tears include surgical repair by adhering edges of a tear with sutures or other similar methods. Meniscectomy is the most common treatment, and involves the partial or total removal of the meniscus, depending on the severity of the tear. However, meniscectomy has many drawbacks, including increasing contact stresses due to the reduction of contact area, as shown in FIGS. 7A-7B. Meniscectomies have been suggested to lead to the progression of osteoarthritis in the knee due to these changes in the joint.

Another known treatment for meniscus tears is a meniscal allograft. An allograft replaces the patient's natural meniscus with one from a donor. The donor meniscus is surgically implanted using sutures, and involves securing the implant by pulling the sutures through drilled bone tunnels in the tibia and tying the sutures together on the distal end as shown in FIG. 8. Although an allograft is associated with better outcomes than meniscectomy, allografts have many drawbacks. Allografts are known to shrink and undergo collagen remodeling, compromising mechanical strength. Other drawbacks include a high failure rate due to secondary tears, inability to stop the progression of osteoarthritis, limited number of available grafts, size matching, high cost, immunological concerns (e.g., risk of rejection of the donor's tissue), and risk of disease transmission.

Because of the limited number of available donor tissues for allografts and the drawbacks of performing a meniscectomy, a variety of artificial meniscus implants have been proposed. However, known artificial implants that have been used clinically suffer many drawbacks, including premature failure due to weakness of the artificial implant structure. Another common problem with some artificial meniscus implants is their free floating nature, which does not allow for the secure fixation of the implant in relation to the tibial surface of the knee and can cause the implant to extrude or slip from its intended joint space.

Accordingly, the disclosed embodiments are directed to overcoming these and other problems.

SUMMARY

Disclosed herein are embodiments of an artificial meniscus that address the shortcomings of conventional devices and surgical techniques. Methods of making and implanting an artificial meniscus implant are also disclosed herein. An artificial meniscus implant includes an arc-shaped body including a polymer material and having a peripheral edge, an interior edge, and first and second horns positioned opposing ends of an arc-shaped length of the body. The artificial meniscus may include at least one first fiber. The at least one first fiber may be embedded in the arc-shaped body and extending along at least a portion of the arc-shaped length of the body. The at least one first fiber may include a first end portion having a first interconnected fiber structure protruding beyond the first horn of the arc-shaped body. The at least one first fiber may include a second end portion having a second interconnected fiber structure protruding beyond the second horn of the arc-shaped body. The artificial meniscus implant may also include at least one second fiber embedded in the arc-shaped body and extending along at least a portion of a radial width of the arc-shaped body between the peripheral edge and the interior edge.

Some embodiments include a first horn extension made of the polymer material and a second horn extension made of the polymer material. The first horn extension may cover at least a first portion of the first interconnected fiber structure proximate the first horn. The second horn extension may cover at least a first portion of the second interconnected fiber structure proximate the second horn. The first horn extension and the second horn extension may include elongated polymer members that embed the interconnected fiber structure or hollow, elongated, polymer members.

In some embodiments, the first end portion and the second end portion each have a diameter approximately between 1 mm and 5 mm extending along a length of each respective fiber.

In some embodiments, the first interconnected fiber structure and the second interconnected fiber structure each include at least four fibers.

In some embodiments, the at least one second fiber includes a peripheral attachment portion protruding beyond the peripheral edge and having one or more attachment loops.

In some embodiments, the polymer material includes a hydrogel that is at least 20% polyvinyl alcohol by weight.

In some embodiments, the tensile strength of the at least one circumferential fiber may be at least 19 MPa. In some embodiments, the tensile strength of the at least one radial fiber may be at least 4 MPa.

In some embodiments, the artificial meniscus may have a minimum fiber tear-out force of 660N. In some embodiments, the artificial meniscus may have a minimum shear strength of 60N. In some embodiments, the artificial meniscus may have a compressive modulus of less than 1.2 MPa.

According to some embodiments, the artificial meniscus implant may include a plurality of first fibers wherein a first subset of the plurality of first fibers are aligned in parallel proximate a central portion of the body, a second subset of the plurality of first fibers converge proximate the first horn, and a third subset of the plurality of first fibers converge proximate the second horn.

According to some embodiments, the at least one second fiber may be a single continuous fiber in a curved orientation extending from the peripheral edge towards the interior edge and forming one or more attachment loops protruding from beyond the peripheral edge.

Methods of making an artificial meniscus are also disclosed herein. The methods include placing an embedded portion of at least one first fiber in a first bulk polymer gel such that a first and second non-embedded portion of the at least one first fiber protrudes beyond the first bulk polymer gel, the at least one first fiber configured to extend along at least a portion of an arc-shaped length of a body of the implant. The method may include causing the first bulk polymer gel to harden into a solid state to form a first intermediate component. The method may include causing a second bulk polymer gel to harden into a solid state to form a second intermediate component of the artificial meniscus. The method may include coating at least one second fiber in a second bulk polymer gel, the at least one second fiber configured to extend along at least a portion of a radial width of the body between a peripheral edge and an interior edge of the body. The method may include attaching the at least one second fiber to the second intermediate component. The method may include arranging the first and second intermediate components within a meniscus-shaped mold and surrounding the first and second intermediate components with a third bulk polymer gel within the meniscus-shaped mold, and causing the third bulk polymer gel to harden into a solid state to form an integral artificial meniscus implant.

According to some embodiments, the method may include braiding the first and second non-embedded portions of the at least one first fiber, at least partially coating the first and second non-embedded portions of the at least one first fiber with a fourth bulk polymer gel, and causing the fourth bulk polymer gel to harden into a solid state to form hollow or fiber-embedding, elongated polymer members.

According to some embodiments, attaching the at least one second fiber to the second intermediate component may include suturing the at least one second fiber through the second intermediate component. In some embodiments, the method may include forming loops with the at least one second fiber that protrudes beyond a peripheral edge of the second intermediate component.

According to some embodiments, the first bulk polymer gel, the second bulk polymer gel, the third bulk polymer gel, and the fourth bulk polymer gel may be made of a hydrogel including polyvinyl alcohol.

Methods of implanting artificial menisci are also disclosed herein. The methods include inserting a first interconnected fiber extension of at least one first fiber extending from a body portion of a meniscus implant into a first bone tunnel of a first bone of a patient. The first interconnected fiber extension may be at least partially covered with a polymer coating disposed between the first bone and the first interconnected fiber extension within the first bone tunnel. The method may include inserting a second interconnected fiber extension of the at least one first fiber extending from the body portion of the meniscus implant into a second bone tunnel of the first bone of the patient. The second interconnected fiber extension may at least be partially covered with a polymer coating disposed between the first bone and the first interconnected fiber extension within the second bone tunnel. The method may include immobilizing the meniscus implant by attaching each of the first interconnected fiber extension and the second interconnected fiber extension to a respective adjacent bone, wherein the attachment may include an attachment method selected from tying the first interconnected fiber extension to the second interconnected fiber extension, affixing each of the first interconnected fiber extension and the second interconnected fiber extension to respective endobuttons implanted into the respective adjacent bone, and affixing each of the first interconnected fiber extension and the second interconnected fiber extension to respective interference screws implanted into the respective adjacent bone.

According to some embodiments, the method may include suturing a peripheral edge of the body portion of the meniscus implant to adjacent bone through one or more attachment loops protruding from beyond the peripheral edge.

DESCRIPTION OF DRAWINGS

The device is explained in even greater detail in the following drawings. The drawings are merely exemplary to illustrate the structure of garments and certain features that may be used singularly or in combination with other features. The drawings are not necessarily drawn to scale.

FIG. 9A shows a top down view of an embodiment of an artificial meniscus.

FIG. 9B shows a top down, cross sectional view of an embodiment of an artificial meniscus, showing the circumferential fibers.

FIG. 9C shows a top down, cross sectional view of an embodiment of an artificial meniscus, showing the non-circumferential fibers.

FIG. 10A shows a side cross sectional view across a width of an embodiment of an artificial meniscus.

FIG. 10B shows a side cross sectional view across a width of an embodiment of an artificial meniscus, showing the circumferential fibers.

FIG. 10C shows a side cross sectional view across a width of an embodiment of an artificial meniscus, showing the non-circumferential fibers.

FIG. 11 shows a peripheral side cross sectional view of an embodiment of an artificial meniscus, showing the circumferential fibers.

FIG. 12 shows a top-down, cross sectional view of an embodiment of an artificial meniscus, showing a non-circumferential fiber.

FIG. 13 shows a top down, cross sectional view of an embodiment of an artificial meniscus, showing a non-circumferential fiber forming peripheral loop members.

DETAILED DESCRIPTION

Figure 1B:
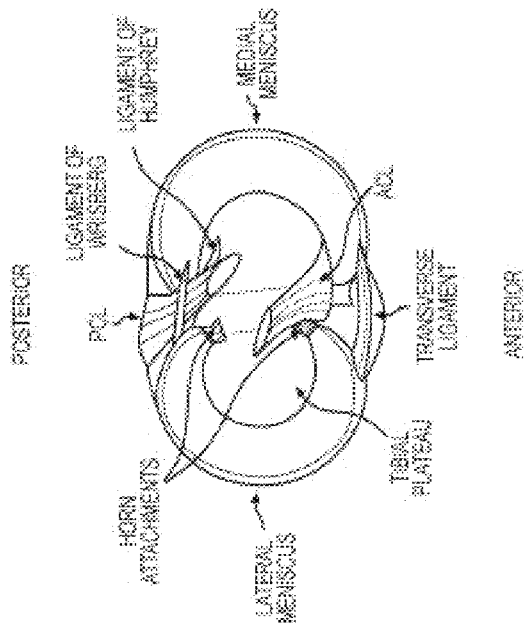
FIGS. 1A-1B shows the anatomy of the knee and the anatomy of the meniscus, respectively. Also shown are associated ligaments within the knee joint and the anterior and posterior horn attachments of the meniscus.
Figure 1A:
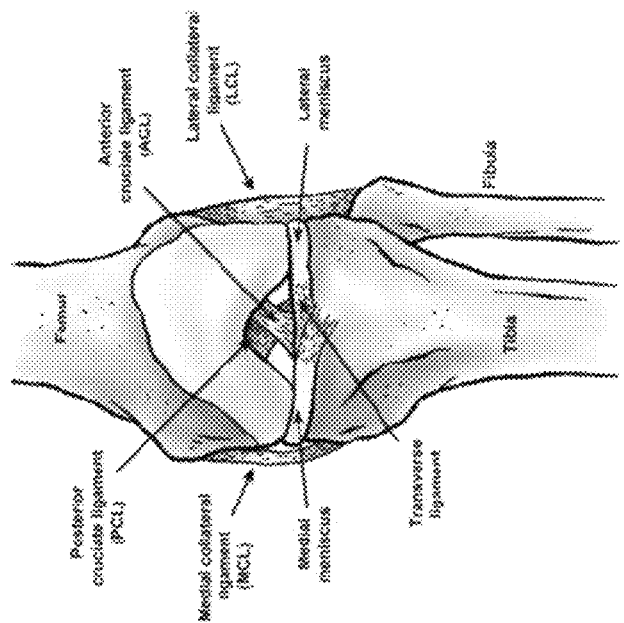
Figure 2:
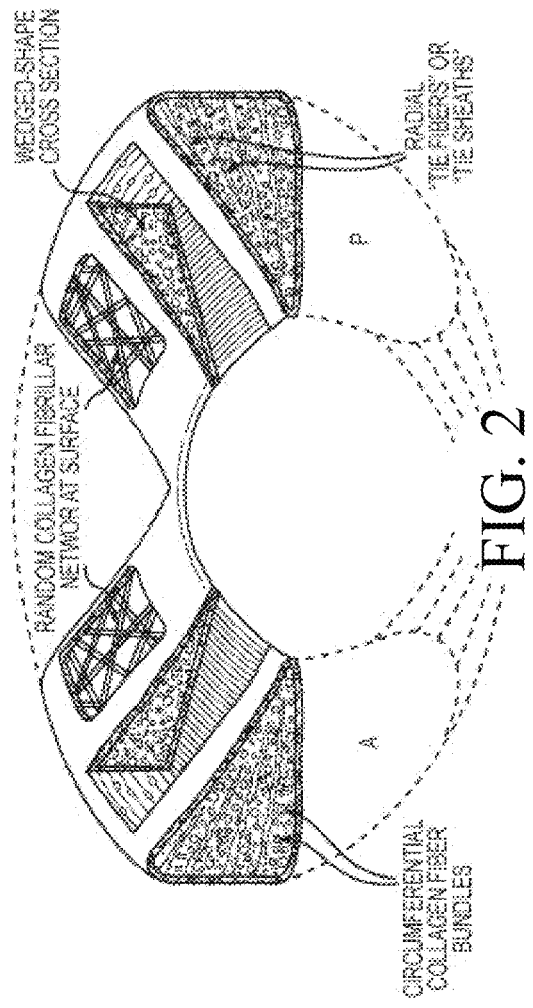
FIG. 2 shows the collagen fiber structure of the meniscus. A random network is at the surface while circumferential and radial fibers are in the deeper tissue layers.
Figure 3B:
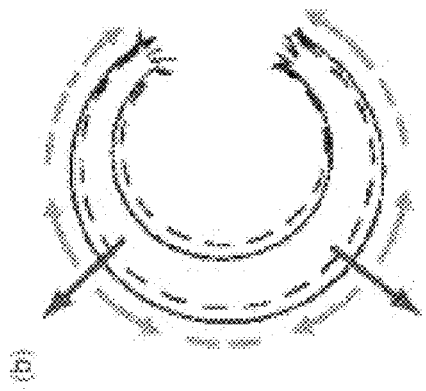
FIGS. 3A-3B shows the loading of the meniscus from the side (a) and from above showing hoop stress development and radial displacement.
Figure 3A:
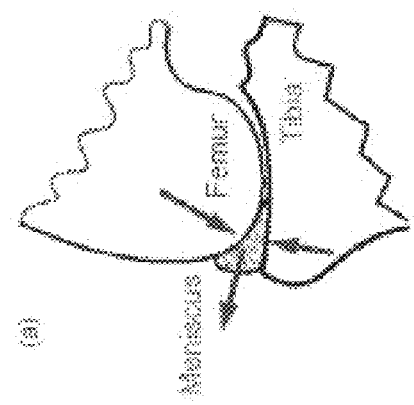
Figure 4:
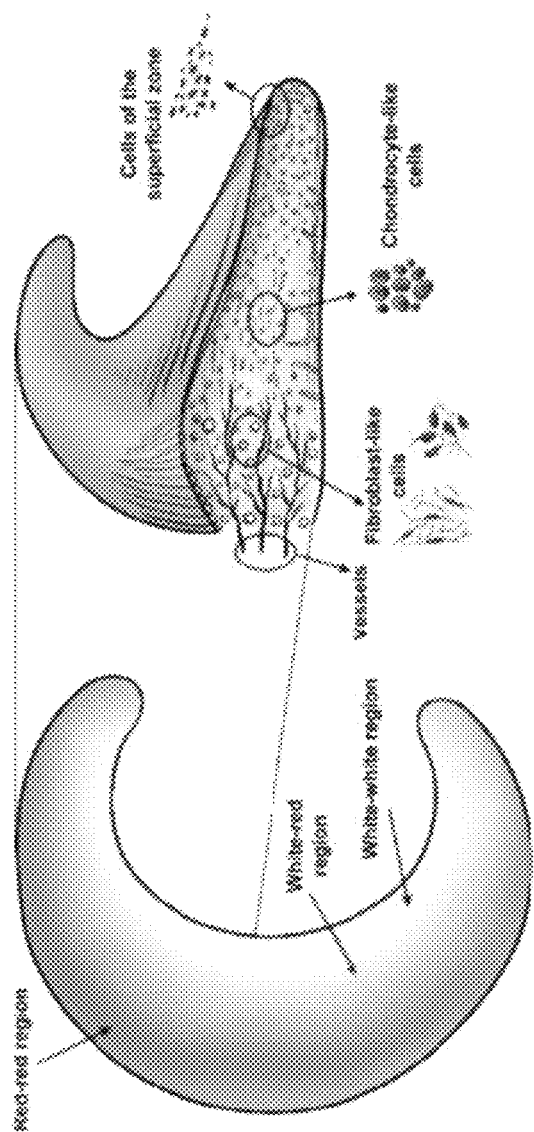
FIG. 4 shows the vascularization of the meniscus. The peripheral red region has vasculature and nerves and central white region does not.
Figures 5A, 5B, 5C, 5D, 5E, 5F, 5G:
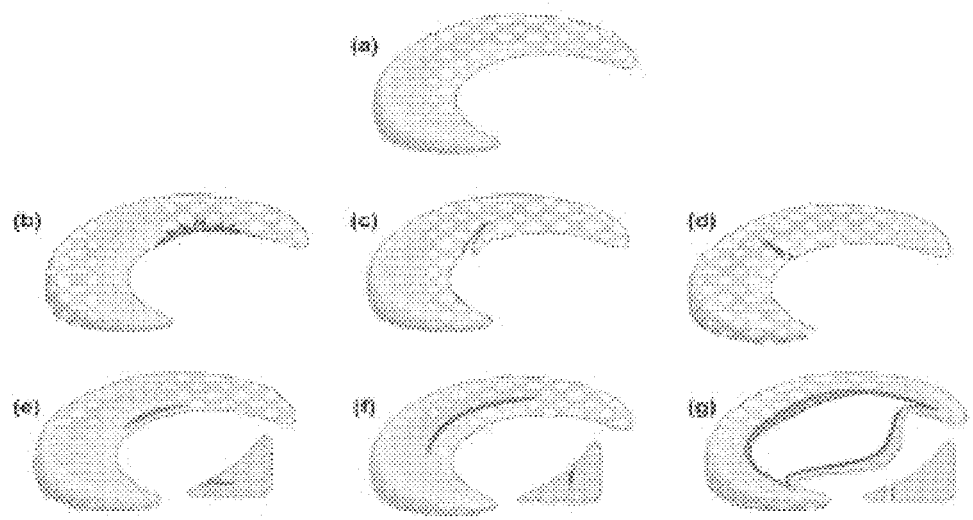
FIGS. 5A-5G show meniscal tear patterns. The healthy meniscus (a) can experience complex/degenerative (b), oblique (c), radial (d), horizontal (e), and longitudinal (f) tears. A longitudinal tear passing through the entire thickness results in a bucket-handle tear (g).
Figure 6:
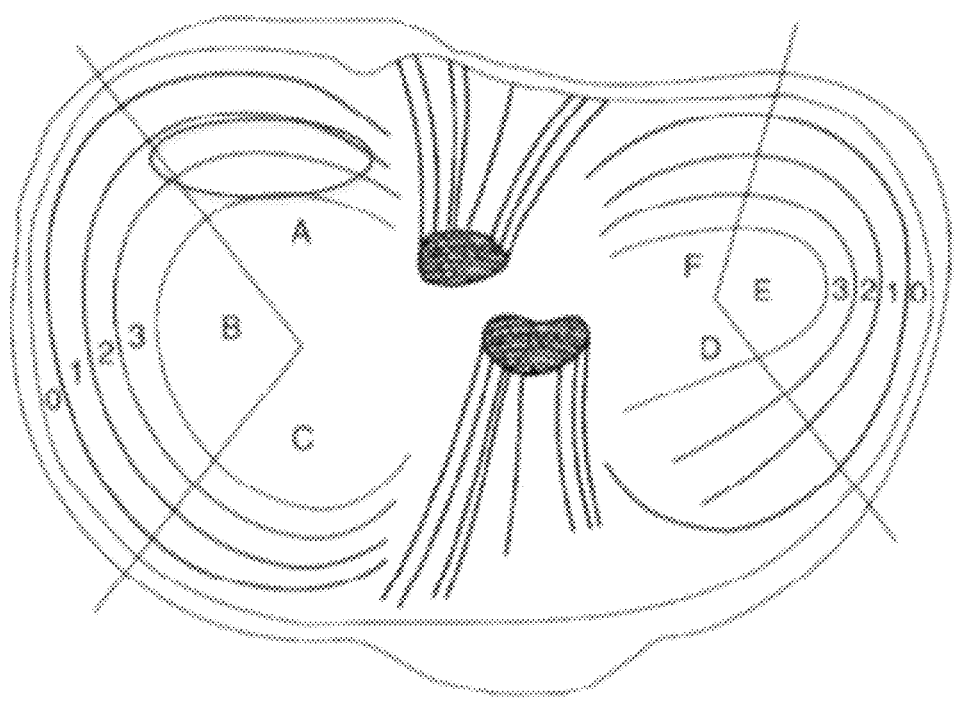
FIG. 6 shows areas of the meniscus where most traumatic tears occur, as indicated by circle A.
Figures 7A, 7B:
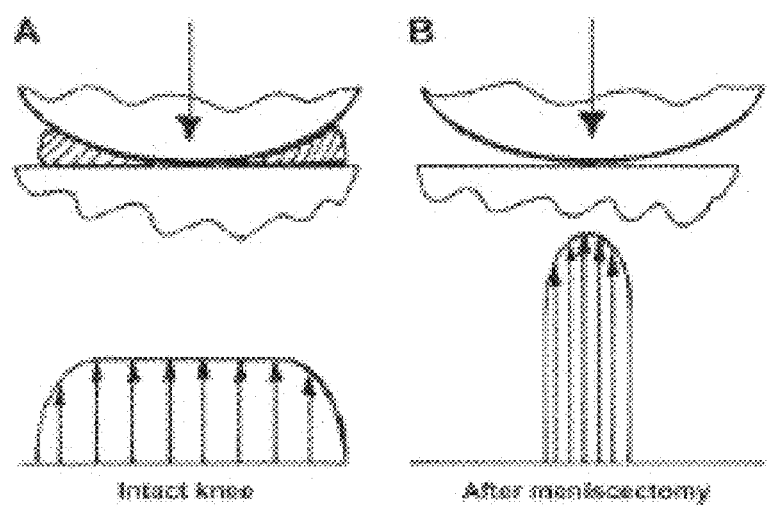
FIGS. 7A-7B shows the contact stress on the tibial plateau for an intact knee (A) is concentrated over a smaller area and increases in magnitude following a meniscectomy (B).
Figure 8:
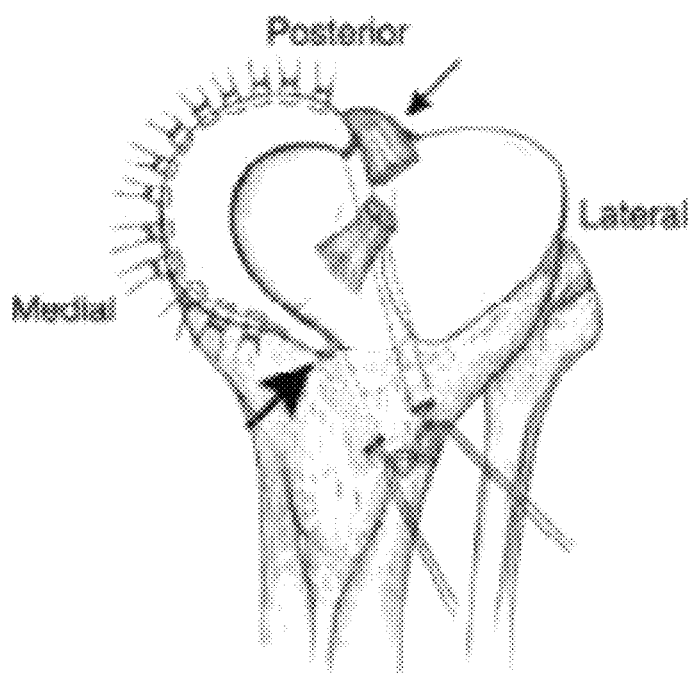
FIG. 8 shows an attachment method of a meniscus allograft.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

The artificial meniscus of the present disclosure will now be described. All directional and orientation terminology refer to a patient in a standing position. Orientation with respect to the artificial meniscus embodiments disclosed herein will include such terms as peripheral, interior, anterior, posterior, inferior, and superior. The anatomical term "anterior" means the feature in question is designed to be positioned adjacent to the front side of the subject's body. Reference is made to the artificial meniscus 2 of FIG. 9A to demonstrate the positioning of the various anatomical terminology. For example, the anterior horn 4 will be positioned such that it is adjacent to the patella on the front side of the subject's knee. Conversely, the anatomical term "posterior" means the feature in question is designed to be positioned adjacent to the rear side of the subject's body. For example, the posterior horn 6 will be positioned such that it is farther from the patella than the anterior horn. A vertical axis (also referred to herein as the Z-axis) can he visualized extending superiorly from the inferior surface 16. For reference, anterior and posterior horn axes, A-A and P-P can be visualized extending perpendicularly to the Z-axis, through the center of (and at a normal to) the respective anterior horn surface 8 and posterior horn surface 10, as shown in FIG. 9A.

The peripheral edge, or peripheral surface 12 of an artificial meniscus 2 refers to the side that, when viewing the arc-shaped structure from a top-down perspective, extends along the outside of the arc-shape, between the anterior horn axis A-A and the posterior horn axis P-P. Conversely, the interior edge, or interior surface 14 of an artificial meniscus 2 indicates the side that, when viewing the arc-shaped structure from a top-down perspective, extends along the inside of the arc-shape, between the anterior horn axis A-A and the posterior horn axis P-P. References to the width, w, of the artificial meniscus indicate a horizontal measurement between the peripheral surface 12 and the interior surface 14 (extending from a point on the interior surface 14 across the shortest distance possible to an oppositely positioned point on the peripheral surface 12, that is, extending along a normal line to the curve of the interior surface 14 across to an oppositely positioned point on the peripheral surface 12). The width of the artificial meniscus can vary depending upon the anterior to posterior positioning of the point of measurement, as well as the inferior to superior positioning of the point of measurement. The "radial" direction indicates a direction extending away from the center of convergence of all widths that extend between the peripheral surface 12 and the interior surface 14. For example, the non-circumferential fibers 28 shown in FIG. 9C extend in radial directions.

Reference is now made to FIG. 10A to describe additional anatomical terminology used herein to describe embodiments of artificial meniscus 2. The terms "inferior" and "superior" indicate orientations in the vertical direction. An inferior side, inferior edge, or inferior surface 16 of artificial meniscus 2 is lower than the superior side, superior edge, or superior surface 18 of artificial meniscus 2, for example. References to the height, h, of the artificial meniscus indicate a vertical measurement between the inferior and superior surfaces. The height of the artificial meniscus may vary depending upon the peripheral to interior positioning of the point of measurement, as well as the anterior to posterior positioning of the point of measurement. Again, all directional and orientation terminology refer to a patient in a standing position.

Figures 14A, 14B, 14C:
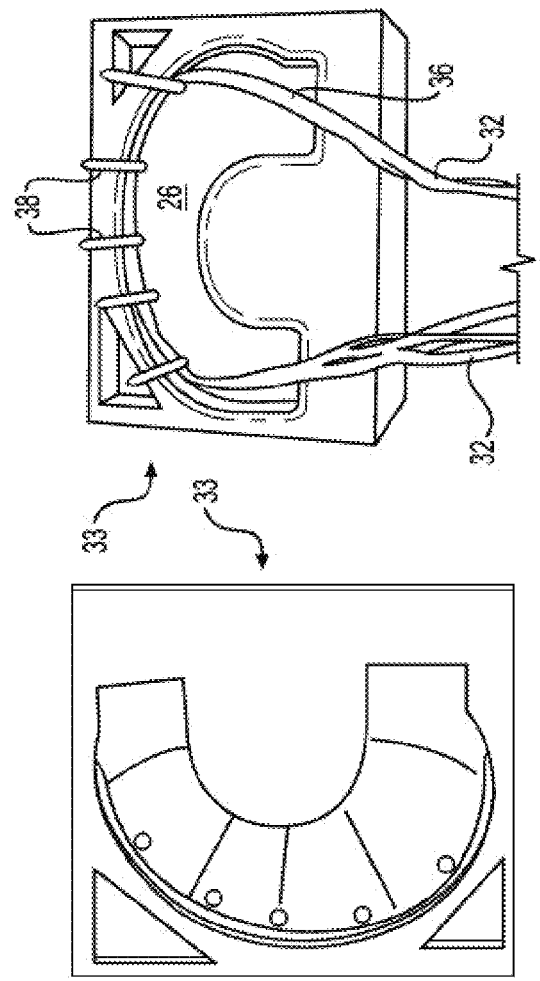
FIGS. 14A-14G show steps of a processing method for the fabrication of a meniscus shaped article.

The artificial meniscus embodiments disclosed herein are generally arc-shaped or C-shaped when viewed from a top-down perspective. However, this is not meant to imply any particular degree of symmetry. In fact, the artificial meniscus embodiments disclosed herein can be slightly asymmetrical (in that the width near one horn can be different than the width near the other horn). In some embodiments, the curve of the peripheral and interior surfaces 12, 14 may extend all the way to tips of anterior and posterior horns 4, 6, such that the entire exterior surface of the artificial meniscus 2 is curved. In other embodiments, the horns 4, 6, may be defined by anterior and posterior horn extensions 20 and 22, as shown in FIG. 14G. In some embodiments, horn extensions 20 and 22 may be defined by polymer extensions configured to cover circumferential fiber ends 32 and protect circumferential fiber ends 32 from excessive wear at the fiber to bone interface of a patient. In some embodiments, horn extensions 20 and 22 may extend into respective bone tunnels of a patient. In some embodiments, horn extensions 20 and 22 may extend into respective bone plugs or keyhole/slot cutouts of a patient, which may provide a tight interference fit to fix the implant into position in a patient. Horn extensions 20 and 22 may be configured to protect the circumferential fiber ends 32 from wear at the bone tunnel interface and may be made of the same polymer material as artificial meniscus 2. Horn extensions 20 and 22 may directly interface with the fiber ends 32 and effectively fill in any gaps in the fiber material with polymer material. According to some embodiments, the polymer material of horn extensions 20 and 22 may effectively integrate with the circumferential fiber ends 32 during the curing process to fill in any gaps in the fiber material. An example of horn extensions 20 and 22 is provided in FIG. 14G. Referring back to FIG. 10A, the superior surface 18 of the artificial meniscus 2 is generally concave, whereas the inferior surface 16 is relatively flat, as shown in FIG. 10A, or at least less curved than the superior surface 18. Some curvature of the inferior surface 16 may exist on a large or small scale depending upon the particular needs of the implant or subject. The height of meniscus 2 is larger at the peripheral surface 12 than the interior surface 14.

The artificial meniscus embodiments disclosed herein are reinforced by fibers 24, 28 that extend within the polymer material 26 of the meniscus 2. Some of the fibers are oriented and aligned so that they can convert the compressive forces into tensile hoop stresses to dissipate the load. To accomplish this, one or more fibers may be circumferentially aligned with the peripheral surface 12 or the interior surface 14 of the meniscus 2, as shown in FIG. 9B, to mimic the circumferential collagen fibers in the natural menisci. Advantageously, the ends 32 of the circumferential fibers 24 that are embedded in polymer material 26 extend out of the meniscus 2 at the anterior and posterior horns 4, 6 to provide attachment points for affixing to the bone. Affixing the ends 32 of the circumferential fibers 24 to the bone helps to prevent dislocation from the joint space under load like the ligaments of the native meniscus. According to some embodiments, prior to affixing ends 32 of the circumferential fibers to the bone, ends 32 may be coated with a polymer gel. The gel may be hardened into a solid state to form hollow or fiber-embedding, elongated horn extensions 20 and 22 that cover the ends 32 of the circumferential fibers. Horn extensions 20 and 22 may integrate with the circumferential fiber ends and act to fill in gaps in the fiber material, improving the strength of the circumferential fiber ends 32, and increasing resistance of the circumferential fiber ends to fraying and wear at the bone to fiber interface. Additionally, in some embodiments, the circumferential fiber ends 32 may also be interconnected to form ends 32A that improve overall attachment fiber strength and resistance to wear/fraying at the bone/fiber interface by keeping the fibers integrated together. An example meniscus 2 having interconnected ends 32A and horn extensions 20 and 22 is shown in FIG. 14G. According to some embodiments the interconnected ends 32A may be provided by braiding individual fibers of circumferential fiber ends 32 together to form interconnected ends 32A, as shown in FIG. 14G. According to some embodiments, the ends 32 of the circumferential fibers may have a diameter approximately between 1 mm and 5 mm extending along a length of each respective fiber to advantageously interface with a surgically made bone tunnel in the bone of the patient receiving the implant. However, circumferential fibers may be of any diameter, and may vary in diameter along the length of the respective fiber in order to provide increased reinforcement in areas most commonly experiencing meniscal tears. According to some embodiments, ends 32 of the circumferential fibers may be tapered to aid in inserting the ends 32 into surgically formed bone tunnels for attachment of the artificial meniscus implant 2 to the patient.

Figure 15:
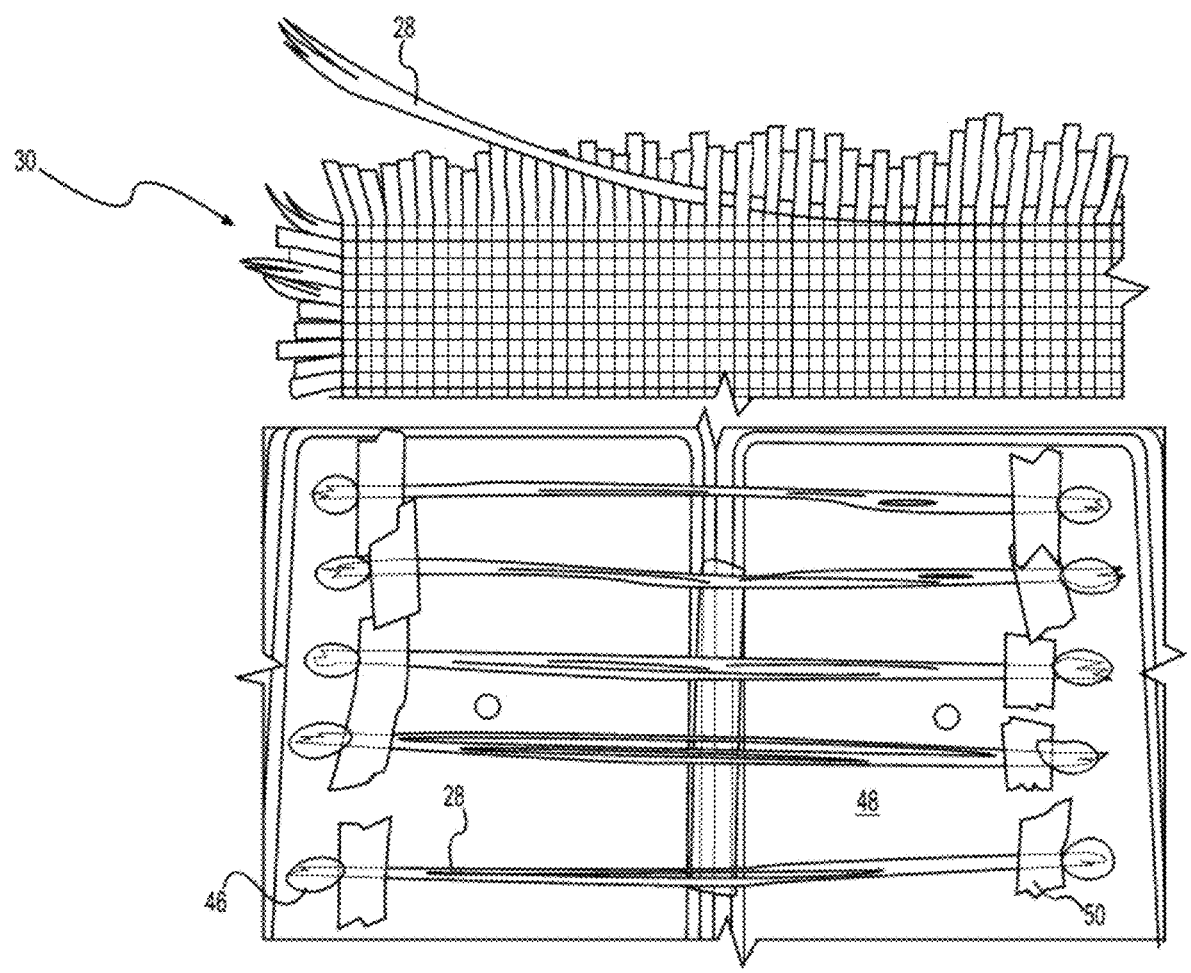
FIG. 15 shows steps of a processing method for the fabrication of a meniscus shaped article.

Since the natural meniscus also has interwoven radial fibers to provide structural integrity, the polymer material 26 of the artificial meniscus 2 is provided with one or more non-circumferential fibers 28, as shown in FIG. 9C, to give the implant radial strength. In some embodiments, the non-circumferential fibers 28 are oriented radially, between the peripheral and interior surfaces 12, 14. As shown in FIG. 15, the non-circumferential fibers could come in the form of a woven sheet 30 that spans across the cross-sectional area of the meniscus 2. This woven sheet 30 would provide strength in all directions and limit implant deformation, as well as provide structural integrity and hold the entire construct together to better avoid tears, ruptures, and any further propagations. Advantageously, the non-circumferential fibers may be implemented as a continuous fiber sewn through the implant in a back-and-forth spline (e.g., curve) shape from peripheral edge 12 towards the interior edge 14 so that loops extending from peripheral edge 12 of the implant were made with the non-circumferential fibers 28. The spline configuration of non-circumferential fibers 28 provides numerous advantages over woven sheet 30, including better integration of the fiber with polymer material 26. Other advantages include the possibility of forming external peripheral loops 28C extending from peripheral edge 12, as shown in FIG. 13.

External peripheral loops 28C may be provided to advantageously allow for a surgeon to suture the peripheral edge 12 of meniscus 2 to bone fixation points of the patient in a manner similar to an allograft procedure, allowing for greater attachment strength and positioning in the joint space compared to previous implants, many of which provide no means of affixing an implant to bones of the patient, let alone provide both attachment at the horns 4, 6, and the peripheral edge 12. The inclusion of external peripheral loops 28C may also advantageously improve implant fixation. For example, external peripheral loops 28C may act to prevent the implant 2 from shifting towards the femoral condyle center of a patient, where the force exerted in the joint is greatest, which may improve the longevity of the implant. According to some embodiments, unlike circumferential fibers 24, which extend out of anterior and posterior horns 4, 6, the non-circumferential fibers may be fully encapsulated within polymer material 26. Fully encapsulating fibers within the polymer material helps to prevent peeling away of the fibers from the implant. However, as described with respect to FIG. 13, in some embodiments external peripheral loops 28C may be provided which are not fully encapsulated within polymer material 26. In order to maintain proper positioning of the implant and a high degree of strength, the peripheral loops 28C may be relatively small in relation to the embedded portion of non-circumferential fibers 28, for example, approximately 5% of the total length of the non-circumferential fibers 28 may be used to form peripheral loops 28C, although the total length percentage of non-circumferential fibers 28 used to form peripheral loops 28C may vary in different embodiments.

Figures 17A, 17B, 17C:
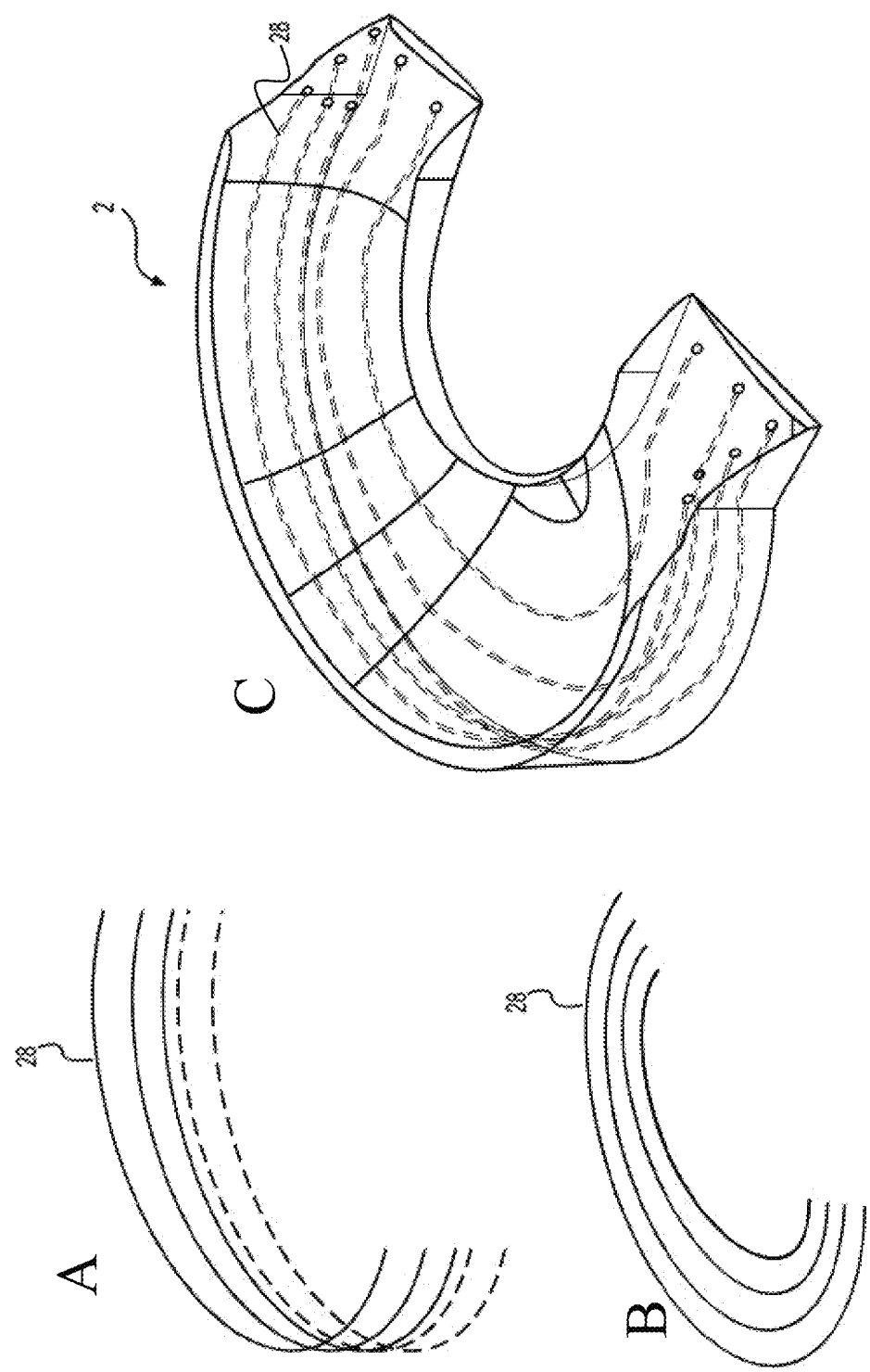
FIGS. 17A-17C shows an exemplary layout and shape of the peripheral fiber groupings (A), bulk fiber groupings (B), and an example of each fiber placement within the implant (C).
Figures 18A, 18B, 18C, 18D, 18E:
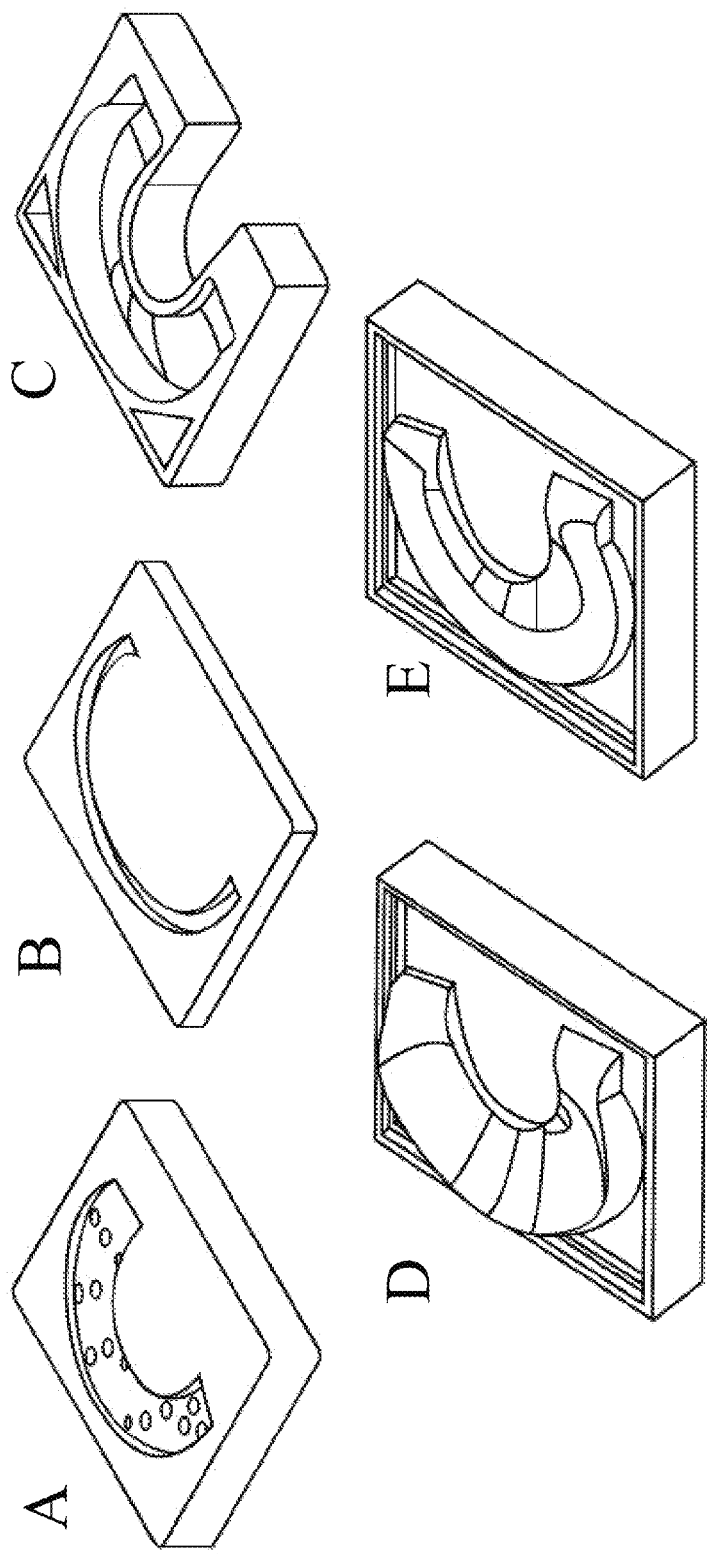
FIGS. 18A-18E depict an inferior circumferential fiber mold (A), superior circumferential mold (B), the final mold (C), a superior offset stamp (D), and an inferior offset stamp (E).

As shown in FIG. 9B, multiple circumferential fibers 24 can be spaced between the peripheral and interior edges 12, 14 of the artificial meniscus 2. The number of circumferential fibers 24 spaced between the peripheral and interior edges 12, 14, of the artificial meniscus 2 can vary widely, and is not meant to limit the scope of the disclosure. The circumferential fibers 24 can be evenly spaced from one another, or unevenly spaced from one another. In some embodiments, the density of the circumferential fibers 24 in the peripheral to interior direction may increase moving toward or away either the peripheral or interior surfaces 12, 14 of the artificial meniscus. The degree of spacing of the circumferential fibers as they exit the anterior and posterior horns may vary. At least one circumferential fiber 24 may be provided within the artificial meniscus implant 2 in order to provide increased strength in the circumferential direction. However, it may be advantageous to include multiple circumferential fibers 24 within the body of artificial meniscus implant 2 to reinforce areas of the implant more prone to tears. For example, FIGS. 17A-17C show an artificial meniscus implant 2 with seven circumferential fibers 24 distributed throughout the body of implant 2. Three of the circumferential fibers are spaced vertically (along the Z-axis) and four fibers are spaced horizontally from each other in order to provide reinforcement throughout the entire artificial meniscus implant 2.

The circumferential fibers 24 exit the artificial meniscus 2 at locations adjacent to the anterior and posterior horns. In some embodiments, the circumferential fibers 24 can converge as they approach the anterior and posterior horns 4, 6, of the artificial meniscus, as shown in FIG. 9B (that is, the peripheral to interior spacing of the circumferential fibers 24 decreases as the fibers approach the horns). The degree of convergence can vary by embodiment, and in some, the circumferential fibers 24 may maintain a constant degree of spacing as they extend through the meniscus 2 from the anterior horn 4 to the posterior horn 6. In some embodiments, a first subset of the circumferential fibers 24 may be aligned in parallel at a central portion of the body of artificial meniscus implant 2. A second subset of the circumferential fibers 24 may converge proximate the first horn (e.g., anterior horn 4), and a third subset of circumferential fibers 24 may converge proximate the second horn (e.g., posterior horn 6). It may be advantageous for fibers to converge proximate horns 4, 6 because these areas of the artificial meniscus implant experience a majority of the compressive load. According to some embodiments, a majority of circumferential fibers 24 may converge at the posterior horn (e.g., implant 2 may have a higher density of circumferential fibers 24 at the posterior horn), which is known to experience the majority of tears in patients.

Figure 16:
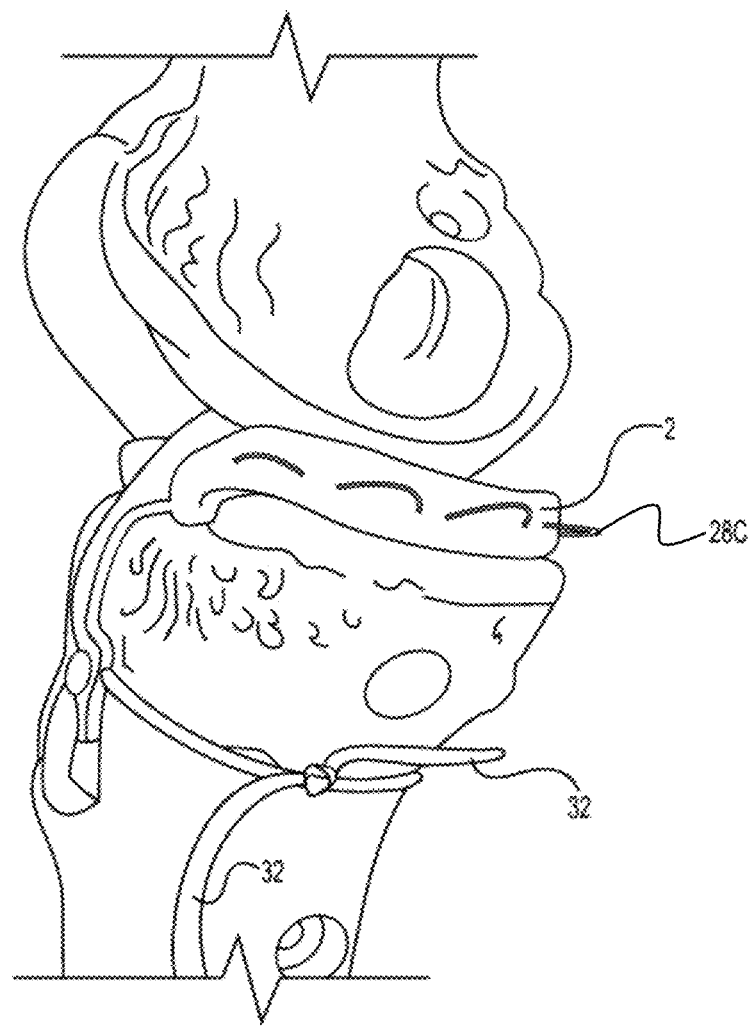
FIG. 16 shows an exemplary attachment method of the artificial meniscus to bone. In some embodiments, the ends of circumferential fibers may be tied to each other on the outside of the bone.

Advantageously, at the edges of the meniscus 2, each exiting circumferential fiber may be individually covered in polymer material 26 in order to reduce the chance of delamination and fiber pull out. The circumferential fibers 24 are affixed to nearby bone structures or surgical implants. For example, the ends 32 of the circumferential fibers, shown in FIGS. 9B, 14F, and 14G, may be pulled through a surgically formed bone tunnel, and affixed at the opposite end of the bone tunnel by tying it to a endobutton, the endobutton being wider than the bone tunnel and including a loop for stringing the fiber therethrough. Alternatively, or in addition, the circumferential fibers 24 can be affixed to the adjacent bones using interference screws, such as those used in allograft fixation surgeries. In some embodiments, the circumferential fibers 24 may be pulled through separate bone tunnels and knotted directly to each other. FIG. 16 shows ends 32 of the circumferential fibers 24 being tied together around a bone model. According to some embodiments, the ends 32 of circumferential fibers 24 may be attached to bone with the use of suture anchors. An anchor portion of the suture anchor may be screwed into or otherwise attached to the tibia near horns 4, 6, of implant 2. The ends 32 of circumferential fibers may then be attached to the suture portion of the suture anchor. According to some embodiments, the ends of circumferential fibers 24 may be attached to bone using an endobutton without the use of a bone tunnel. For example, the endobutton may be implanted into the bone using an interference fit as commonly implemented with a bone plug method of fixation. In some embodiments, the ends 32 of circumferential fibers 24 may be fixed to bone using a key-hole technique, in which an aperture of a particular shape is made in the bone, and horn extensions 20 and 22 are shaped to precisely fit the aperture made in the bone with a tight interference fit. However, fixation of ends 32 may be accomplished by using any other common bone fixation technique known in the art.

In some embodiments, in addition to affixing circumferential fiber ends 32 to bone, meniscus 2 may be further attached by suturing or sewing external peripheral loops 28C (e.g., loops formed by non-circumferential fibers 28) to bone. The addition of external peripheral loops 28C may further increase durability of meniscus implant 2 as well as promote tighter fixation to the desired implant area.

In addition to spacing multiple circumferential fibers 24 in the peripheral to interior direction, multiple circumferential fibers 24 can be spaced from each other in the Z-direction. This may be especially advantageous near the peripheral surface 12, as shown in FIG. 10B, to provide additional reinforcements for converting compressive forces into tensile hoop stresses to dissipate the load and reduce radial extrusion across the height of the implant. The number of circumferential fibers 24 spaced between the inferior and superior surfaces of the artificial meniscus can vary widely, and is not meant to limit the scope of the disclosure. The circumferential fibers 24 can be evenly spaced from one another in the Z-direction, or unevenly spaced from one another. In some embodiments, the density of the circumferential fibers 24 in the Z-direction may increase moving toward or away either the inferior surface 16 or superior surface 18 of the artificial meniscus 2. In some embodiments, the outermost (most peripherally positioned) circumferential fibers 24 are on, adjacent to, or immediately interior to the peripheral surface 12 (positioned just far enough into the artificial meniscus 2 to allow the fibers to be penetrated by the polymer material 26). As such, the polymer filled fibers are palpable and visible from the peripheral surface 12 of the artificial meniscus, as shown in FIG. 11. This positioning of the circumferential fibers 24 facilitates distribution of hoop stress throughout the implant and reduces radial extrusion across the height (e.g., Z-direction) of the implant. An example of circumferential fiber spacing along the Z-direction of the implant and the horizontal direction may be seen in FIGS. 17A-17C.

In some embodiments, the combined ultimate tensile strength of the at least one circumferential fiber 24 is at least 19 MPa. Although the ultimate tensile strength of natural, anisotropic meniscal tissue varies by region, the mean maximum stress within the meniscus has been found to be 11-19 MPa in the circumferential direction and 2-4 MPa in the radial direction. Therefore, in some embodiments, the artificial meniscus 2 will have an ultimate circumferential tensile strength of at least 19 MPa in the circumferential direction and at least 2 MPa in the radial direction so that it is able to withstand the same maximum stresses as a natural meniscus, which is a parameter almost all previous developers of artificial meniscus implants have failed to address. The circumferential tensile stress value may be taken from a sample that is circumferentially oriented around the periphery of the implant, since the periphery is where the tensile hoop stresses develop during loading to resist radial deformation. The ultimate circumferential tensile strength is additive in that each circumferential fiber 24 contributes a fraction of the combined measurement. For example, ten evenly sized circumferential fibers (of equivalent materials and densities) might give an ultimate circumferential tensile strength of 20 MPa. In that scenario, each fiber might contribute to 2 MPa of the ultimate circumferential tensile strength. Of course, the individual contributions to the ultimate stress measurement may vary if the sizes, materials, or other properties vary between fibers.

The tensile modulus of the natural meniscus can vary on location between about 50 MPa to 300 MPa circumferentially. Therefore, in some embodiments, the artificial meniscus 2 has a tensile modulus is at least 50 MPa in the circumferential direction to limit deformation and extrusion.

The artificial meniscus embodiments also include one or more non-circumferential fibers 28 extending in non-circumferential directions. In some embodiments, such as the one shown in FIG. 9C, multiple non-circumferential fibers 28 extend in a radial direction, from a position adjacent the interior surface 14 to a position adjacent the peripheral surface 12. The radially extending, non-circumferential fibers 28 can be spaced across the artificial meniscus 2 between the anterior horn 4 and the posterior horn 6. The number of radially extending non-circumferential fibers 28 spaced from each other between the anterior horn 4 and the posterior horn 6 can vary widely, and is not meant to limit the scope of the disclosure. The radially extending non-circumferential circumferential fibers 28 can be evenly spaced from one another, or unevenly spaced from one another. In some embodiments, the density of the non-circumferential fibers 28 may vary. For example, the density of radially extending non-circumferential fibers 28 may be higher (i.e., the measured distance between fibers may be lower) at a position adjacent to the posterior horn 6 than the anterior horn 4. Increased density of radially extending non-circumferential fibers 28 near the posterior horn 6 advantageously mimics the distribution of strengths of the intact meniscus. Furthermore, increased density of radially extending non-circumferential fibers 28 near the posterior horn 6 may also be used to further reinforce and strengthen the posterior region of the implant corresponding to the region the intact meniscus experiences the most tears. In some embodiments, non-circumferential fibers 28 may be interconnected. Interconnected fibers may advantageously provide increased strength and also increased resistance to friction fatigue failure. In some embodiments, the fibers may be interconnected by braiding individual non-circumferential fibers 28 together.

Some embodiments, such as those shown in FIG. 12 and FIG. 13, may include a single non-circumferential fiber 28 that extends back and forth in an at least partially curved line (e.g., a spline shape). The non-circumferential fiber 28 may extends from positions near the peripheral edge 12 of the artificial meniscus 2 across the width of the artificial meniscus 2 to positions near the interior edge 14 of the artificial meniscus 2, then back again. The embodiment of FIG. 12 shows a non-circumferential fiber 28 that includes relatively long straight segments extending directly across the width of meniscus 2, curving relatively sharply at positions adjacent to the peripheral edge 12 and the interior edge 14. The embodiment of FIG. 13, by contrast, shows a non-circumferential fiber 28 that spans a longer distance near the peripheral and interior edges 12, 14, curving relatively gently then backtracking over shorter straight segments as it crosses the width of the meniscus 2. In some embodiments, a non-circumferential fiber 28 can curve continuously as it moves back and forth between the peripheral and interior edges 12, 14. Varying patterns of curvature of the non-circumferential fiber 28 are considered to be within the scope of the disclosure, and may have different advantages depending upon the footprint and magnitude of the load they are intended to support. As further shown in FIG. 13, according to some embodiments, a non-circumferential fiber 28 can extend out of the peripheral edge 12 of the artificial meniscus 2 to form a plurality of external peripheral loops 28C. External peripheral loops 28C may be provided to advantageously allow for a surgeon to suture the peripheral edge 12 of meniscus 2 to bone fixation points of the patient in a manner similar to an allograft procedure, allowing for greater attachment strength compared to previous implants. Another advantage of using external peripheral loops 28C to increase fixation of the implant is that surgeons are generally familiar with the attachment procedure due to the similarity to an allograft attachment procedure. In addition, external peripheral loops 28C may act to prevent the implant 2 from shifting towards the femoral condyle center of a patient, which may improve the longevity of the implant due to preventing the implant from shifting to the location at which the femur exerts the most load.

Some embodiments of artificial meniscus 2 can include multiple non-circumferential fibers 28 spaced from each other in the Z-direction, as shown in FIG. 10C. The non-circumferential fibers 28 may be oriented horizontally (that is, perpendicularly to the Z-axis), such as the lowermost non-circumferential fiber 28a adjacent inferior surface 16. Alternatively, or in addition, the non-circumferential fibers 28 may be oriented at one or more angles to the inferior surface 16, traveling superiorly as they extend from the interior to the periphery of the artificial meniscus 2. For example, as shown in FIG. 10C, the uppermost non-circumferential fiber 28b, which is positioned adjacent the superior surface 18, extends away from interior surface 14 at an angle, and remains adjacent the superior surface 18 as it curves upward to terminate at a point adjacent both the superior surface 18 and the peripheral surface 12. The number of non-circumferential fibers 28 spaced from each other in the Z-direction (between the inferior and superior surfaces of the artificial meniscus) can vary widely, and is not meant to limit the scope of the disclosure. The non-circumferential fibers can be evenly spaced from one another in the Z-direction, or unevenly spaced from one another. In some embodiments, the density of the circumferential fibers in the Z-direction may increase moving toward or away from either the inferior or superior surfaces 16, 18 of the artificial meniscus 2.

In some embodiments, the non-circumferential fibers 28 are embedded in polymer material 26 as close to the superior surface 18 as possible without substantially increasing friction between the superior surface 18 and the adjacent bone of the subject. The non-circumferential fibers 28 can follow the curvature of the superior surface. Likewise, inferiorly positioned non-circumferential fibers 28 can be positioned adjacent the inferior surface 16 of the artificial meniscus yet still embedded in the polymer material. The non-circumferential fibers 28 can be embedded within the polymer material 26 as close as possible to the inferior surface 16 without causing an unfavorable amount of friction between the inferior surface and the adjacent bone of the patient, and can follow any curvature of the inferior surface 16, should it exist.

In an alternative embodiment, such as the one shown in FIG. 15, the non-circumferential fibers can be woven together as part of a larger reinforcement sheet 30. The woven sheet of fibers can be positioned perpendicularly to the Z-axis, or may tilt at an angle relative to the Z-axis. Regardless of the tilt, the reinforcement sheet 30 may extend from a peripheral to interior direction across artificial meniscus 2, as well as from an anterior to posterior direction. The direction of the warp and weft of the reinforcement sheet 30 is not critical to the function of the device. In some embodiments, strips of the reinforcement sheet 30 could be cut and laid in a radially spaced arrangement across the width of the meniscus 2. Furthermore, the reinforcement sheet 30 that includes non-circumferential fibers need not necessarily be woven, but could alternatively be a non-woven sheet, a knit sheet 30, or any other textile patterning without veering from the scope of this disclosure.

The combined ultimate tensile strength of the at least one non-circumferential fiber 28 is at least 1 MPa, and, in some embodiments, at least 4 MPa. Although the ultimate tensile strength of natural anisotropic meniscal tissue varies by region, the mean maximum strength of the meniscus has been found to be around 4 MPa radially. The ultimate tensile strength of the non-circumferential fibers 28 is additive in that each non-circumferential fiber contributes a fraction of the combined measurement. For example, ten evenly sized non-circumferential fibers (of equivalent materials and densities) might give an ultimate tensile strength of 6 MPa. In that scenario, each non-circumferential fiber 28 might contribute to 0.6 MPa of the ultimate non-circumferential tensile stress. Of course, the individual contributions to the ultimate tensile strength measurement may vary if the sizes, materials, or other properties vary between fibers.

Then natural tensile modulus in the radial direction can be about 20 to about 70 MPa. As such, the tensile modulus of the implant in the radial direction should be at least 20 MPa to limit deformation and extrusion.

Generally, the polymer material 26 is elastic and relatively soft. A wide range of compressive moduli have been reported for the natural menisci and their values are dependent on strain level, loading rate, and test type. Studies have reported values for the compressive modulus of the human meniscus to be from 0.30 to 1.16 MPa under unconfined compression at a physiologic strain and strain rate. This means that under an unconfined testing protocol, a meniscal implant material should have a modulus of at least 0.30 MPa in a physiologic strain range. Like the tensile modulus specification, the upper limit for the compressive modulus is not critical since metal materials have been used in spacer devices and have moduli much greater than 1.13 MPa. Therefore, the modulus for a flexible prosthetic meniscus should remain within an order of magnitude of the natural meniscus at less than or equal to 100 MPa.

Tensile loads develop consistently during gait with each step taken, and have been estimated to peak around 50N during simulated motion at the anteromedial meniscal insertion site and about 65N±25 under joint loading in the posterior horn attachment site. Since the meniscus would realistically experience only one of the attachment site maximums, these values indicate a tensile load of about 90N would be a worst-case value for most human individuals. Therefore, the artificial meniscus 2 can sustain at least 100 N of tensile load for 1000 cycles under cyclic tension testing. There should also be no significant changes in ultimate tensile strength or tensile modulus following these cycles.

Shear forces, in particular shear forces parallel to the tibial plateau, are commonly experienced in the knee and has been identified as a leading failure mode including horizontal tearing and delamination of implants. It was observed in vivo that the highest shear experienced by the knee during common daily activities occurs while descending stairs or performing a leg press and knee extension exercise, and is equivalent to 35% a person's bodyweight. A $50^{th}$ percentile body mass male above the age of 20 corresponds to a shear force of 290 N using equation 3. By using the area of the inferior surface of the implant (793 mm$^2$) and the area of a cylindrical sample used for the test (78.5 mm$^2$), the force may be converted to a shear stress of 30 N using Equation 4. The maximum daily activity shear force is seen while a subject descends a staircase, so a threshold test for meniscus implant 2 is whether there are no macroscopically observable tearing or delamination following completion of 40,000 cycles of 30 N shear stress to simulate a year of use.

$$m \times g \times BW \times MSL = 2{,}300 \text{ N}$$

Mass of Average Male: m=85 kg; Acceleration of Gravity: g=9.8; Body Weight Multiplier: BW=3.46; Medial Side Load Transmission: MSL=0.8

$$12 \frac{\text{steps}}{\text{flight}} \times 9 \frac{\text{flights}}{\text{day}} \times 365 \frac{\text{days}}{\text{year}} \times 0.5 \frac{\text{leg compression}}{\text{step}} \times 2 \frac{\text{force spikes}}{\text{leg compression}} = 40{,}000 \text{ force spikes.}$$

Equation 1: Daily compression force

Equation 2: Daily compression cycle number.

$$m \times g \times BW = 290 \text{ N}$$

Mass of Average Male: m=85 kg; Acceleration of Gravity: g=9.8; Body Weight Multiplier: BW=0.35

Equation 3: Daily and extreme shear force in knee.

$$m \times g \times BW = 290 \text{ N}$$

Shear Force in Knee: S=290 N; Implant Inferior Surface Area: A=793 mm$^2$; Cylindrical Sample Radius: R=5 mm Equation 4: Shear force in knee conversion to shear force on sample.

The polymer material 26 can be any biocompatible polymer that meets the criteria outlined above. In some embodiments, the polymer material 26 is a hydrogel, such as polyvinyl alcohol (PVA) or a PVA copolymer. In some embodiments, the polymer material can be of a single molecular weight of PVA, at a set concentration and number/duration of freeze-thaw cycles used in the setting/curing process. PVA hydrogel properties can vary significantly when these parameters are changed. The number of freeze-thaw cycles has been shown to have little effect on properties after five or six cycles. Certain embodiments of the polymer material of the artificial meniscus disclosed herein have a higher concentration of PVA than the previous PVA-hydrogel implants, which likely contributes to improved strength and limited deformation.

Alternatively, the polymer material 26 can be a polyurethane material or a polycarbonate material (including co-polymers of polyurethane or polycarbonate). In some embodiments, the polymer material can be a naturally occurring polymer. For example, the polymer material can be collagen, a collagen co-polymer, or a mixture of collagen and a synthetic polymer.

The mesh network of the polymer material 26 may include pores up to a size of 250 microns. In some embodiments, the pores are a product of freeze thaw cycling, and are not large enough to permit cell ingrowth. In other embodiments, larger pores are included to permit cell ingrowth.

Fibers 24, 28 can be formed of a synthetic material. In some embodiments, the fibers include an aramid material. In some embodiments, the fibers include a poly-paraphenylene terephthalaramide material, such as Kevlar® or Twaron® (of any grade). Some embodiments utilize synthetic materials for the fibers, such as ararmid fibers, PVA fibers, polyurethane fibers, and/or polyethylene terephthalate fibers. Some embodiments utilize naturally occurring materials for fibers, such as, for example, silk fibers, and/or collagen fibers. In some embodiments, different materials can be used for different fibers. In other embodiments, all fibers are formed of the same material. According to some embodiments, rather than using single fibers, multiple fibers forming fiber bundles may be used in place of single strands of fibers as fiber 24, 28.

Advantageously, the polymer material 26 penetrates individual fibers of the circumferential and non-circumferential fibers 24, 28. That is to say, the polymer material 26 infiltrates the fiber network and crosslinks within the fibers, thereby guarding against delamination of the fibers and slippage or tear out of the fibers after implantation. In some embodiments, the fiber material is hydrophilic, or at least somewhat conducive to absorbing water. The hydrophilic properties of the fibers facilitate infiltration of the polymer material 26 into the fiber networks and help to prevent fiber tear out. That being said, an important failure mode to consider and design for is the fibers tearing out of the bulk polymer material during functional loading. Since the average strength of the native meniscus roots is approximately 660N, the artificial meniscus 2 can be designed to withstand this force without failure of the fiber-polymer interface when under physiologic-like loading. As such, the artificial meniscus 2 should have a fiber tear out strength of at least 660 N. Testing this type of loading may include applying tension to exterior ends 32 of the circumferential fibers 24 while the artificial meniscus is held stationary.

Modular processing techniques may be undertaken to form different parts or layers of a meniscus-shaped article 44 prior to any final processing steps that yield the implantation-ready artificial meniscus. FIGS. 14A-14G show different phases of an example process of fabricating the artificial meniscus 2. FIG. 14A shows a CAD model of the artificial meniscus 2. FIG. 14B shows a mold 33 for the artificial meniscus, the mold including holes 34 in the base. Different sets of fibers can be individually coated/penetrated by the bulk polymer precursor material to form intermediate components that are then set and can be arranged and molded together in the meniscus-shaped mold 33. Bulk polymer can be poured around the intermediate components once they are arranged in the mold, in multiple layering and setting steps if needed to accomplish the desired Z-direction layering. In this way, in the completed meniscus-shaped article 44, the bulk polymer material 26 surrounds the circumferential and non-circumferential fibers 24, 28 is a continuous, unitary structure.

In some embodiments, multiple layering and molding/setting steps may be performed to accomplish the layering of fibers and various regions of the meniscus-shaped article. For example, a first, bottom layer of bulk polymer precursor material may be poured first and set into a bottom layer of polymer material 26. Or, alternatively, the mold can be inverted and a top layer of bulk polymer precursor material can be poured first and set.

Separately, fibers may be coated/penetrated with the polymer material 26 and allowed to set. Separately coating the fibers helps to keep the fibers in their intended position during the later molding and layering steps that take place within the mold 33. The fibers, now encapsulated within intermediate components, may be arranged on the bottom or top layer of bulk polymer material. The intermediate component 36 that includes the circumferential fibers 24 can be set in a curved formation. FIG. 14C demonstrates an intermediate component 36 (including circumferential fibers 24 embedded within polymer material) being positioned around rods 38 that are placed within holes 34 around the periphery of mold 33. Alternatively, fibers can be positioned around the rods 38, and then coated in polymer precursor material while positioned between the rods 38 and the peripheral wall of mold 33, so as to form intermediate component 36 in a curved formation within the mold 33 itself. The rods 38 are removed before any further addition of polymer material to the mold to prevent any holes in the final meniscus-shaped article. As shown in FIG. 14D, a second layer of bulk polymer precursor material can be poured over the first intermediate component 36. The second layer of precursor can be set into a second layer of polymer material 26. Note that the intermediate molding and setting processing steps can be repeated as many times as necessary to achieve the desired layout, meniscal shape, and layering of fibers.

Second intermediate components including the non-circumferential fibers 28 can be separately embedded in polymer material, or at least partially embedded in polymer material. FIG. 15 shows non-circumferential fibers 28 intended for radial alignment as shown in FIG. 9C. The fibers may be removed from a woven mat and at least the ends may be dipped in polymer precursor 46 in order to make the fibers easier to manipulate (in some embodiments, the entire fiber could be dipped in polymer material or the dipping of the fibers may be skipped entirely). Optionally, the fibers 28 may then affixed to a surface 48 via tape 50 or some other affixation means, and the polymer precursor may be allowed or induced to set/cure. These non-circumferential fibers 28 can then be threaded through the implant 2 using a sewing needle. According to some embodiments, the fibers 28 may not be cured prior to threading the fibers 28 through implant 2, and the combined fibers 28 and implant 2 may be allowed to set or cure together after the fibers 28 have been sewn into the implant 2. A radial fiber guide fixture may be used as a guide to sew the non-circumferential fibers 28 into the implant at the desired height and make loops that are evenly spaced along the peripheral edge 12. Preferably, sewing starts on the peripheral edge 12 of the posterior horn 4, and makes loops through the body of meniscus 2 to the point on the opposite edge (e.g., interior surface 12) perpendicular to the sewing stroke starting point. FIG. 14F shows the non-circumferential fibers 28 sewn into a spline shape, according to some embodiments. Optionally, sewn non-circumferential fibers 28 may form external peripheral loop extensions 28C, as shown in FIG. 13. Previous methods of constructing meniscus 2 involved laying non-circumferential fibers 28 within a second layer of polymer material 26 as a second intermediate component layer and curing the first intermediate component together with second intermediate component to form the meniscus shaped article 44. However, the previous method had the distinct drawback that the non-circumferential fibers 28 would shift during the molding process. Advantageously, sewing the non-circumferential fibers 28 into the meniscus shaped article 44 provides much greater control over the shape and position of the non-circumferential fibers 28, allowing the non-circumferential fibers 28 to retain a radial fiber orientation, improving the overall strength and resistance to delamination of meniscus 2.

Figure 14E:
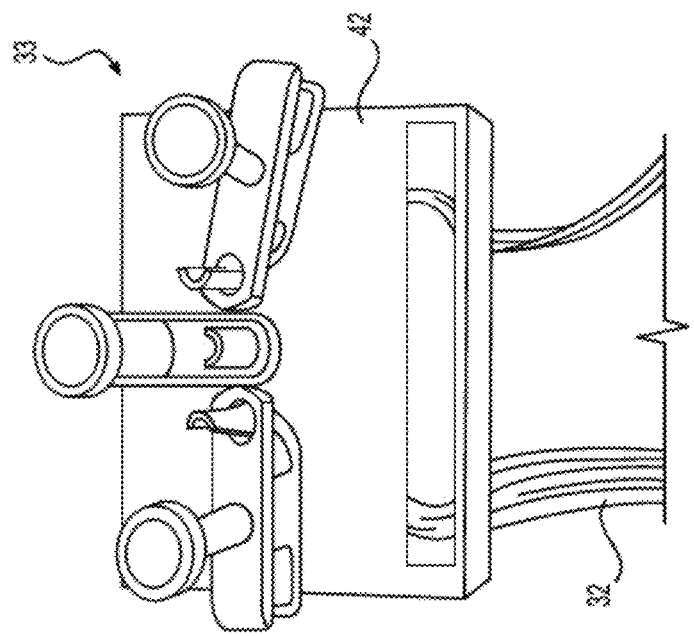
Figure 14D:
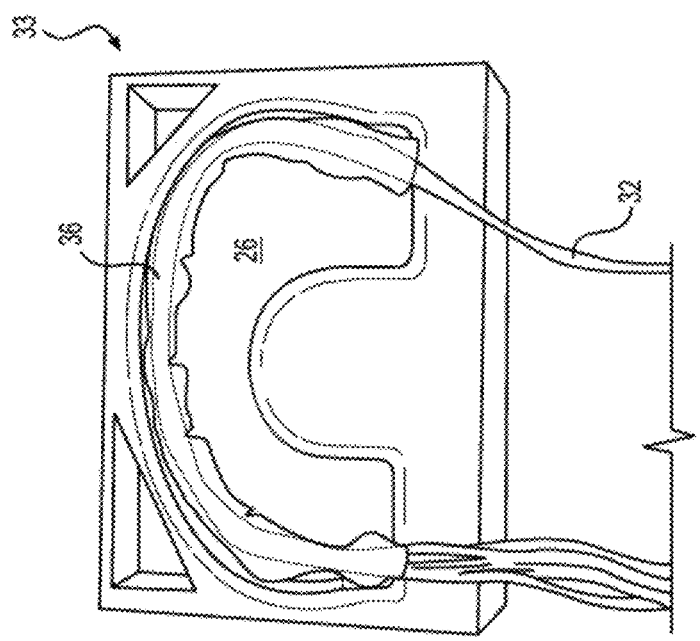
Figure 14G:
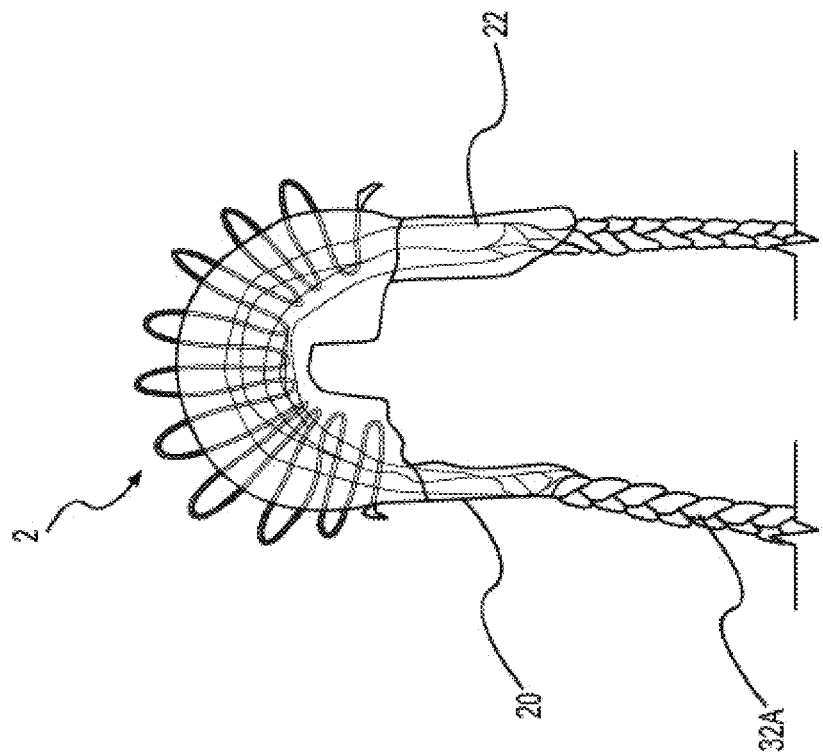
Figure 14F:
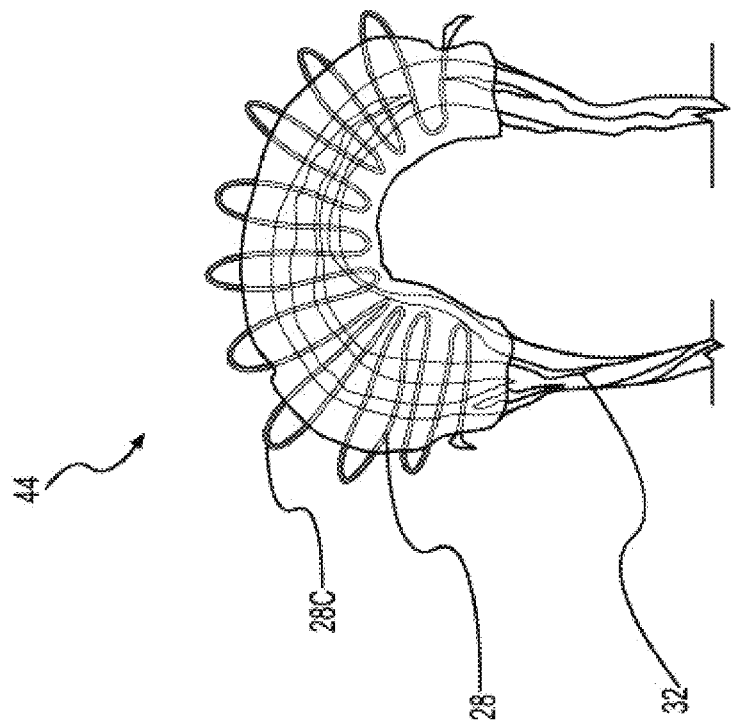

A final, top layer of polymer precursor can be poured over the second intermediate component and the top 42 of the mold 33 clamped onto the mold 33 for the final setting step shown in FIG. 14E. The meniscus shaped article 44 is then removed from the mold and subjected to any final processing techniques, as shown in FIGS. 14F and 14G. Final processing steps may be undertaken to convert the meniscus-shaped article 44 into an artificial meniscus 2 ready for implantation. These final processing steps can include smoothing of surfaces, sewing of non-circumferential fiber 28 into the implant, incorporation of biocompatibility coatings, interconnecting and/or braiding fiber ends 32 into interconnected fiber ends 32A (e.g., see FIG. 14G), capturing the fiber ends 32 into a sheath (e.g., posterior and anterior horn extensions 20 and 22, shown in FIG. 14G), sterilization, and packaging the device into a double barrier pouch. Example molds used for the production process described in FIGS. 14A-14G are shown in FIGS. 18A-18E. FIGS. 18A-18E show an inferior circumferential fiber mold (A), superior circumferential mold (B), the final mold (C), a superior offset stamp (D), and an inferior offset stamp (E). The molds shown in FIGS. 18A-18E may be used to form the meniscus shaped article 44.

In some embodiments, a single polymer precursor material is used to set the intermediate components and form the layers of polymer material. The process of setting the polymer precursor includes freeze and thaw cycling. In a preferred embodiment, the single polymer is polyvinyl alcohol. Varying concentrations by weight of polyvinyl alcohol may be used to make different portions of the implant. For example, the body of the artificial implant may be mostly constructed of polyvinyl alcohol that is about 40% polyvinyl alcohol by weight. The portions of the implant that interface with reinforcement fibers 24, 28 may be made of about 20% polyvinyl alcohol by weight in order to better integrate the fibers 24, 28 into the bulk material body of the artificial meniscus implant 2. According to some embodiments, the body of artificial meniscus implant 2 may be constructed of 20% or greater polyvinyl alcohol by weight. In some embodiments, the ends 32 of circumferential fibers 24 and/or the non-circumferential fibers 28 may be coated with an approximately 10% polyvinyl alcohol by weight, which is more malleable and allow for easier manipulation of the ends 32 and/or fibers 24 than if coated with a different weight of polyvinyl alcohol, although higher weight polyvinyl alcohol polymer may be used in certain embodiments.

Methods of implanting the artificial meniscus 2 are also disclosed herein. The methods of implanting may include inserting a first interconnected fiber extension (32A) of at least one circumferential fiber extending from a body portion of an implant 2 into a first bone tunnel or first bone plug of a first bone of a patient. The first interconnected fiber extension may be at least partially covered with a polymer coating that may be disposed between the first bone and the interconnected fiber extension (32C) within the first bone tunnel or first bone plug. The method may include inserting a second interconnected fiber extension (32C) into a second bone tunnel or second bone plug of the first bone of the patient. The second interconnected fiber extension may be at least partially covered with a polymer coating disposed between the first bone and the second interconnected fiber extension within the second bone tunnel or second bone plug. In some embodiments, the polymer coating may be used to form horn extensions (e.g., horn extensions 20 and 22) that may be specially formed to fit into an aperture of a particular shape that is made in the bone with an interference fit (e.g., key-hole technique). The method may include immobilizing the meniscus implant 2 by attaching each of the first interconnected fiber extension 32C and the second interconnected fiber extension 32C to a respective adjacent bone. The attachment may be achieved by a method selected from tying the first interconnected fiber extension to the second interconnected fiber extension (as shown in FIG. 20), affixing each of the first interconnected fiber extension and the second interconnected fiber extension to respective endobuttons implanted into the respective adjacent bone, affixing each of the first interconnected fiber extension 32C and the second interconnected fiber extension 32C to respective interference screws implanted into the respective adjacent bone, and/or affixing each of the first interconnected fiber extension 32C and the second interconnected fiber extension 32C to respective suture anchors, and/or inserting the polymer coating (e.g., horn extensions 20 and 22) into formed apertures in the bone.

Methods of making an artificial meniscus 2 are also disclosed herein. The methods of making the implant may include placing an embedded portion of at least one first fiber (e.g., circumferential fiber 24) in a first bulk polymer gel such that a first and second non-embedded portion of the at least one first fiber protrudes beyond the first bulk polymer gel (e.g., forming ends 32 extending out of horns 4, 6). The at least one first fiber may be configured to extend along at least a portion of an arc-shaped length of a body of the implant (e.g., artificial meniscus implant 2). The method may include causing the first bulk polymer gel to harden into a solid state forming a first intermediate component. The method may include causing a second bulk polymer gel to harden into a solid state to form a second intermediate component of the artificial meniscus. The method may include coating at least one second fiber in a second bulk polymer gel (e.g., non-circumferential fiber 28). The at least one second fiber may be configured to extend along at least a portion of a radial width of the body between a peripheral edge (e.g., peripheral edge 12) and an interior edge (e.g., interior edge 14) of the body. The method may include attaching the at least one second fiber to the second intermediate component, arranging the first and second intermediate components within a meniscus-shaped mold, and surrounding the first and second intermediate components with a third bulk polymer gel within the meniscus-shaped mold. The method may include causing the third bulk polymer gel to harden into a solid state to form an integral artificial meniscus implant.

According to some embodiments, the method may further include braiding the first and second non-embedded portions (e.g., ends 32) of the at least one first fiber (circumferential fiber 24), at least partially coating the first and second non-embedded portions of the at least one first fiber with a fourth bulk polymer gel, and causing the fourth bulk polymer gel to harden into a solid state to form hollow or fiber-embedding, elongated polymer members (e.g., horn extensions 20 and 22).

According to some embodiments, attaching the at least one second fiber to the second intermediate component may include suturing the at least one second fiber through the second intermediate component. The method may further include forming one or more loops (e.g., peripheral loops 28C) that protrude beyond a peripheral edge of the second intermediate component. According to some embodiments, the first bulk polymer gel, the second bulk polymer gel, the third bulk polymer gel, and the fourth bulk polymer gel may each be made of a hydrogel made of polyvinyl alcohol.

Examples of the present disclosure can be implemented according to at least the following clauses:

Clause 1: An artificial meniscus implant comprising: an arc-shaped body comprising a polymer material and having a peripheral edge, an interior edge, and first and second horns positioned proximate opposing ends of an arc-shaped length of the body; at least one first fiber embedded in the arc-shaped body and extending along at least a portion of the arc-shaped length of the body, the at least one first fiber comprising a first end portion having a first interconnected fiber structure protruding beyond the first horn of the arc-shaped body and a second end portion having a second interconnected fiber structure protruding beyond the second horn of the arc-shaped body; and at least one second fiber embedded in the arc-shaped body and extending along at least a portion of a radial width of the arc-shaped body between the peripheral edge and the interior edge.

Clause 2: The artificial meniscus implant of clause 1, wherein the arc-shaped body further comprises: a first horn extension comprising the polymer material, the first horn extension covering at least a first portion of the first interconnected fiber structure proximate the first horn; and a second horn extension comprising the polymer material, the second horn extension covering at least a first portion of the second interconnected fiber structure proximate the second horn, the first horn extension and the second horn extension comprising fiber-embedding, elongated polymer members.

Clause 3: The artificial meniscus implant of clause 2, wherein the first end portion and the second end portion each comprise a diameter between approximately 1 mm and 5 mm extending along a length of each respective fiber.

Clause 4: The artificial meniscus of clause 1, wherein the first interconnected fiber structure and the second interconnected fiber structure each comprise at least four fibers.

Clause 5: The artificial meniscus implant of clause 1, wherein the at least one second fiber comprises a peripheral attachment portion protruding beyond the peripheral edge and having one or more attachment loops.

Clause 6: The artificial meniscus implant of clause 1, wherein the polymer material comprises a hydrogel comprising at least 20% polyvinyl alcohol by weight.

Clause 7: The artificial meniscus implant of clause 1, wherein the tensile strength of the at least one first fiber is at least 19 MPa.

Clause 8: The artificial meniscus implant of clause 1, wherein the tensile strength of the at least one second fiber is at least 4 MPa.

Clause 9: The artificial meniscus implant of clause 1, wherein the at least one first fiber and the at least one second fiber are embedded in the arc-shaped body such that the arc-shaped body has a fiber tear-out force of at least 660N.

Clause 10: The artificial meniscus implant of clause 1, wherein the arc-shaped body has a shear strength of at least 60N.

Clause 11: The artificial meniscus implant of clause 1, wherein the arc-shaped body has a compressive modulus of less than 1.2 MPa in a vertical direction.

Clause 12: The artificial meniscus implant of clause 1, wherein each of the first interconnected fiber structure and the second interconnected fiber structure comprise a tapered end configured for insertion into a respective bone tunnel.

Clause 13: The artificial meniscus implant of clause 1, comprising a plurality of first fibers wherein a first subset of the plurality of first fibers are aligned in parallel proximate a central portion of the body, a second subset of the plurality of first fibers converge proximate the first horn, and a third subset of the plurality of first fibers converge proximate the second horn.

Clause 14: The artificial meniscus implant of clause 1, wherein the at least one second fiber comprises a single continuous fiber in a curved orientation extending from the peripheral edge towards the interior edge and forming at least one loop protruding from beyond the peripheral edge.

Clause 15: A method of making an artificial meniscus implant, the method comprising: placing an embedded portion of at least one first fiber in a first bulk polymer gel such that a first and second non-embedded portion of the at least one first fiber protrudes beyond the first bulk polymer gel, the at least one first fiber configured to extend along at least a portion of an arc-shaped length of a body of the implant; causing the first bulk polymer gel to harden into a solid state to form a first intermediate component; causing a second bulk polymer gel to harden into a solid state to form a second intermediate component of the artificial meniscus; coating at least one second fiber in a second bulk polymer gel, the at least one second fiber configured to extend along at least a portion of a radial width of the body between a peripheral edge and an interior edge of the body; attaching the at least one second fiber to the second intermediate component; arranging the first and second intermediate components within a meniscus-shaped mold; surrounding the first and second intermediate components with a third bulk polymer gel within the meniscus-shaped mold; and causing the third bulk polymer gel to harden into a solid state to form an integral artificial meniscus implant.

Clause 16: The method of clause 15, further comprising: braiding the first and second non-embedded portions of the at least one first fiber; at least partially coating the first and second non-embedded portions of the at least one first fiber with a fourth bulk polymer gel; and causing the fourth bulk polymer gel to harden into a solid state to form fiber-embedding, elongated polymer members.

Clause 17: The method of clause 15, wherein attaching the at least one second fiber to the second intermediate component comprises suturing the at least one second fiber through the second intermediate component, wherein the method further comprises forming one or more loops with the at least one second fiber that protrude beyond a peripheral edge of the second intermediate component.

Clause 18: The method of clause 13, wherein the first bulk polymer gel, the second bulk polymer gel, the third bulk polymer gel, and the fourth bulk polymer gel each comprise a hydrogel comprising polyvinyl alcohol.

Clause 19: A method of implanting an artificial meniscus, comprising: inserting a first interconnected fiber extension of at least one first fiber extending from a body portion of a meniscus implant into a first bone tunnel of a first bone of a patient, the first interconnected fiber extension at least partially covered with a polymer coating disposed between the first bone and the first interconnected fiber extension within the first bone tunnel; inserting a second interconnected fiber extension of the at least one first fiber extending from the body portion of the meniscus implant into a second bone tunnel of the first bone of the patient, the second interconnected fiber extension at least partially covered with a polymer coating disposed between the first bone and the second interconnected fiber extension within the second bone tunnel; and immobilizing the meniscus implant by attaching each of the first interconnected fiber extension and the second interconnected fiber extension to a respective adjacent bone, wherein the attachment comprises an attachment method selected from tying the first interconnected fiber extension to the second interconnected fiber extension, affixing each of the first interconnected fiber extension and the second interconnected fiber extension to respective endobuttons implanted into the respective adjacent bone, and affixing each of the first interconnected fiber extension and the second interconnected fiber extension to respective interference screws implanted into the respective adjacent bone.

Clause 20: The method of clause 19, further comprising suturing a peripheral edge of the body portion of the meniscus implant to adjacent bone through at least one attachment loop protruding from beyond the peripheral edge.

What is claimed is:

1. An artificial meniscus implant comprising:
    an arc-shaped body comprising a polymer material that inhibits cell ingrowth and having a peripheral edge, an interior edge, a first horn, and a second horn positioned proximate opposing ends of an arc-shaped length of the arc-shaped body, the arc-shaped body defining a circumferential direction extending between the first horn and the second horn and a radial direction perpendicular to the circumferential direction;
    a plurality of first fibers embedded in the arc-shaped body and defining a first fiber longitudinal length that extends in the circumferential direction, each of the plurality of first fibers comprising a first end portion having a first interconnected fiber structure protruding beyond the first horn of the arc-shaped body and a second end portion having a second interconnected fiber structure protruding beyond the second horn of the arc-shaped body, wherein the plurality of first fibers are not interconnected within the arc-shaped body; and
    at least one second fiber embedded in the arc-shaped body, each of the at least one second fiber extending along at least a portion of a radial width of the arc-shaped body between the peripheral edge and the interior edge, defining a second fiber longitudinal length that extends in the radial direction, and not in contact with and spaced apart from the plurality of first fibers, the first interconnected fiber structure, and the second interconnected fiber structure.

2. The artificial meniscus implant of claim 1, wherein the arc-shaped body further comprises:
    a first horn extension comprising the polymer material, the first horn extension covering a portion of the first interconnected fiber structure proximate the first horn to seal together each of the plurality of first fibers in the first interconnected fiber structure; and
    a second horn extension comprising the polymer material, the second horn extension covering a portion of the second interconnected fiber structure proximate the second horn to seal together each of the plurality of first fibers in the second interconnected fiber structure.

3. The artificial meniscus implant of claim 2, wherein the first end portion and the second end portion each comprise a diameter between approximately 1 mm and 5 mm extending along a length of each respective fiber.

4. The artificial meniscus implant of claim 1, wherein the first interconnected fiber structure and the second interconnected fiber structure each comprise at least four fibers.

5. The artificial meniscus implant of claim 1, wherein the at least one second fiber comprises a peripheral attachment portion protruding beyond the peripheral edge and having one or more attachment loops.

6. The artificial meniscus implant of claim 1, wherein the polymer material comprises a hydrogel comprising at least 20% polyvinyl alcohol by weight.

7. The artificial meniscus implant of claim 1, wherein a tensile strength of the plurality of first fibers is at least 19 MPa.

8. The artificial meniscus implant of claim 1, wherein a tensile strength of the at least one second fiber is at least 4 MPa.

9. The artificial meniscus implant of claim 1, wherein the plurality of first fibers and the at least one second fiber are embedded in the arc-shaped body such that the arc-shaped body has a fiber tear-out force of at least 660N.

10. The artificial meniscus implant of claim 1, wherein the arc-shaped body has a shear strength of at least 60N.

11. The artificial meniscus implant of claim 1, wherein the arc-shaped body has a compressive modulus of less than 1.2 MPa in a vertical direction.

12. The artificial meniscus implant of claim 1, wherein the arc-shaped body further comprises:
    a tapered first polymeric horn extension covering a portion of the first interconnected fiber structure to protect the plurality of first fibers from abrasion at a first bone tunnel; and
    a tapered second polymeric horn extension covering a portion of the second interconnected fiber structure to protect the plurality of first fibers from abrasion at a second bone tunnel.

13. The artificial meniscus implant of claim 1, wherein a first subset of the plurality of first fibers are aligned in parallel proximate a central portion of the arc-shaped body, a second subset of the plurality of first fibers converge proximate the first horn, and a third subset of the plurality of first fibers converge proximate the second horn.

14. The artificial meniscus implant of claim 1, wherein the at least one second fiber comprises a single continuous fiber in a curved orientation extending from the peripheral edge towards the interior edge and forming at least one loop protruding from beyond the peripheral edge.

15. A method of making an artificial meniscus implant, the method comprising:
    placing an embedded portion of at least one first fiber in a first bulk polymer gel such that a first non-embedded portion and a second non-embedded portion of the at least one first fiber protrudes beyond the first bulk polymer gel, the at least one first fiber defining a first fiber longitudinal length that extends in a circumferential direction of an arc-shaped body of the artificial meniscus implant;
    causing the first bulk polymer gel to harden into a solid state; and
    attaching at least one second fiber to the hardened first bulk polymer gel, wherein each of the at least one second fiber:
        extends along at least a portion of a radial width of the artificial meniscus implant between a peripheral edge and an interior edge,
        defines a second fiber longitudinal length that extends in a radial direction perpendicular to the circumferential direction, and
        is not in contact with and spaced apart from the at least one first fiber.

16. The method of claim 15, further comprising:
    braiding the first non-embedded portion and the second non-embedded portion of the at least one first fiber;
    at least partially coating the first non-embedded portion and the second non-embedded portion of the at least one first fiber with a second bulk polymer gel; and causing the second bulk polymer gel to harden into a solid state to form fiber-embedding, elongated polymer members.

17. The method of claim 15, further comprising:
surrounding the hardened first bulk polymer gel with a second bulk polymer gel within a meniscus-shaped mold; and
causing the second polymer gel to harden into a solid state to form an integral artificial meniscus implant,
wherein attaching the at least one second fiber comprises suturing the at least one second fiber through the integral artificial meniscus implant.

18. The method of claim 15, wherein causing the first bulk polymer gel to harden into a solid state includes forming a first intermediate component;
the method further comprising:
coating the at least one second fiber in a second bulk polymer gel;
causing the second bulk polymer gel to harden into a solid state to form a second intermediate component of the artificial meniscus;
arranging the first intermediate component and the second intermediate component within a meniscus-shaped mold;
surrounding the first intermediate component and the second intermediate component with a third bulk polymer gel within the meniscus-shaped mold; and
causing the third bulk polymer gel to harden into a solid state to form an integral artificial meniscus implant.

19. A method of implanting an artificial meniscus, comprising:
inserting a first interconnected fiber extension of at least one first fiber extending from a body portion of a meniscus implant into a first bone tunnel of a first bone of a patient, the first interconnected fiber extension at least partially covered with a polymer coating disposed between the first bone and the first interconnected fiber extension within the first bone tunnel, wherein the at least one first fiber defines a first fiber longitudinal length that extends in a circumferential direction of an arc-shaped body and at least one second fiber defines a second fiber longitudinal length that extends in a radial direction of the arc-shaped body perpendicular to the circumferential direction, the at least one second fiber is not in contact with and spaced apart from the at least one first fiber;
inserting a second interconnected fiber extension of the at least one first fiber extending from the body portion of the meniscus implant into a second bone tunnel of the first bone of the patient, the second interconnected fiber extension at least partially covered with a polymer coating disposed between the first bone and the second interconnected fiber extension within the second bone tunnel; and
immobilizing the meniscus implant by attaching each of the first interconnected fiber extension and the second interconnected fiber extension to a respective adjacent bone, wherein the attachment comprises an attachment method selected from tying the first interconnected fiber extension to the second interconnected fiber extension, affixing each of the first interconnected fiber extension and the second interconnected fiber extension to respective endobuttons implanted into the respective adjacent bone, or affixing each of the first interconnected fiber extension and the second interconnected fiber extension to respective interference screws implanted into the respective adjacent bone.

20. The method of claim 19, further comprising suturing a peripheral edge of the body portion of the meniscus implant to adjacent bone through at least one attachment loop protruding from beyond the peripheral edge.

* * * * *